United States Patent [19]

Ferri et al.

[11] Patent Number: 6,160,203
[45] Date of Patent: Dec. 12, 2000

[54] DNA STRANDS CODING FOR GLYCEROL-E-PHOSPHATE ACYLTRANSFERASE

[75] Inventors: Stefano Ferri; Toshihiro Toguri, both of Yokohama, Japan

[73] Assignee: Kirin Beer Kabushiki Kaisha, Tokyo-to, Japan

[21] Appl. No.: 09/000,092

[22] PCT Filed: Jul. 3, 1996

[86] PCT No.: PCT/JP96/01844

§ 371 Date: Jan. 26, 1998

§ 102(e) Date: Jan. 26, 1998

[87] PCT Pub. No.: WO97/05246

PCT Pub. Date: Feb. 13, 1997

[30] Foreign Application Priority Data

Jul. 27, 1995 [JP] Japan .................................. 7-192123

[51] Int. Cl.[7] .............................. A01H 5/00; C12N 15/82; C07H 21/04

[52] U.S. Cl. ..................... 800/281; 800/298; 800/289; 435/69.1; 435/419; 435/468; 536/23.2; 536/23.6

[58] Field of Search ................................. 536/23.6, 23.2; 435/69.1, 468, 419; 800/281, 298, 289

[56] References Cited

U.S. PATENT DOCUMENTS 5,516,667 5/1996 Nishizawa ................................ 800/289

FOREIGN PATENT DOCUMENTS 1-235594 9/1989 Japan .
6-504439 5/1994 Japan .
95/14094 5/1995 WIPO .

*Primary Examiner*—Elizabeth F. McElwain
*Attorney, Agent, or Firm*—Foley & Lardner

[57] ABSTRACT

DNA strands having the ability to biotechnologically produce glycerol-3-phosphate acyltransferase (ATase) useful for converting the property of the PG of membrane lipids into that of more chilling resistance, specifically a chimeric gene of glycerol-3-phosphate acyltransferase (ATase) cDNA derived from squash in which the about one-third central region (the site cleaved by Kpn I and Hind III) has been replaced with the corresponding region of spinach ATase cDNA, a cDNA derived from squash in which the about one-sixth central region (the site cleaved by Hind III and Sac I) has been replaced with the corresponding region of spinach ATase cDNA, or a chimeric gene of ATase cDNA derived from spinach in which the about one-third 3'-terminal region (the site cleaved by Kpn I and Eco RI) has been replaced with the corresponding region of squash ATase cDNA are disclosed.

These chimeric genes can express a chimeric ATase which has a higher substrate selectivity to unsaturated fatty acids. The DNA strand is introduced and expressed in a chilling sensitive plant, so that it can afford a plant the chilling resistance higher than that afforded by the ATase gene derived from a known chilling resistant plant.

9 Claims, 3 Drawing Sheets

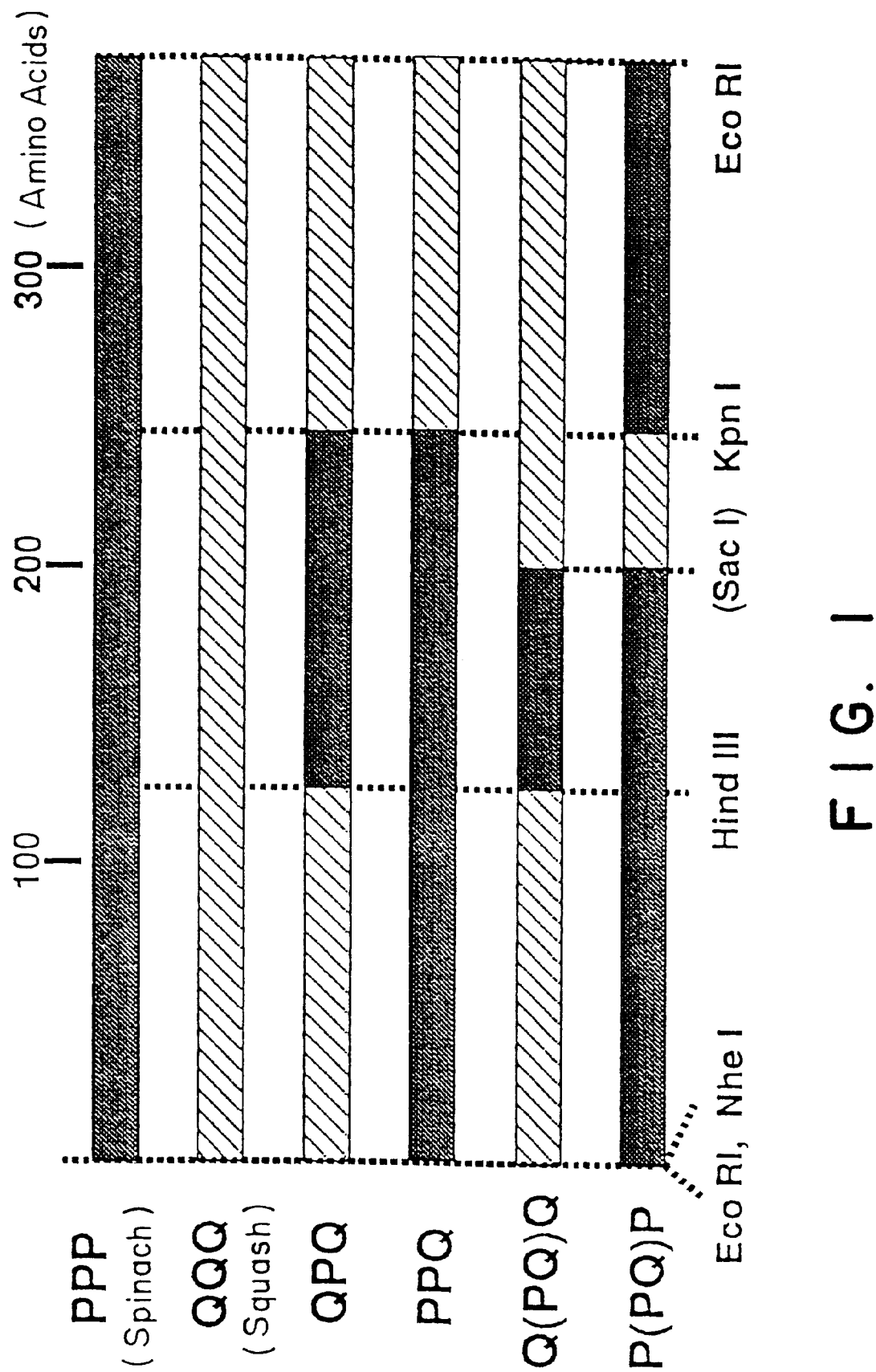
F I G. 1

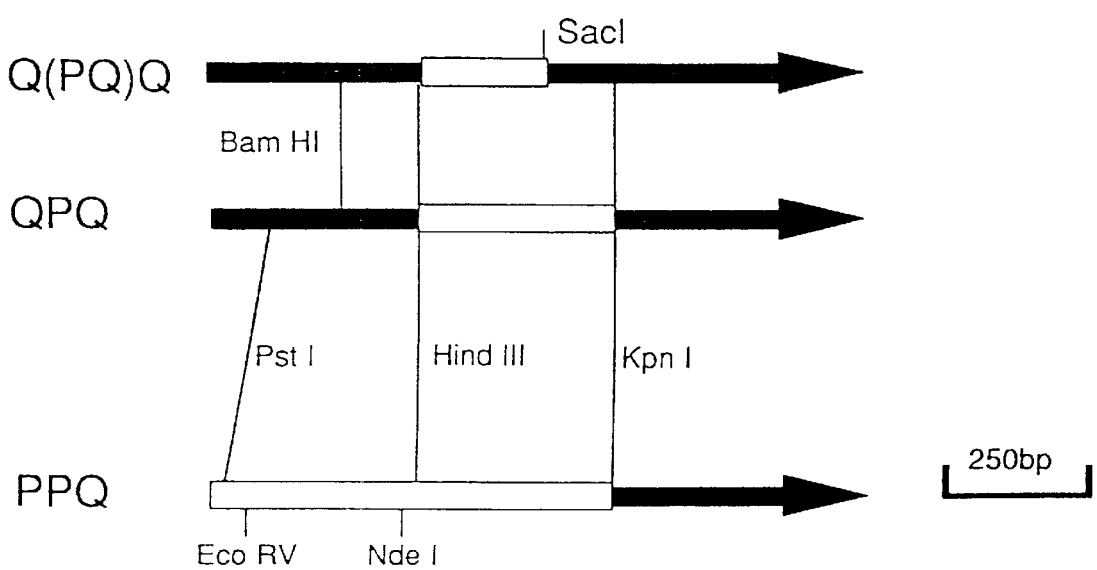
F I G. 3

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
      (A) LENGTH: 1104 base pairs
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: CDS
      (B) LOCATION: 1..1104

(xi) SEQUENCE DESCRIPTION: SEQ ID NO:1:

```
ATG GCT AGC CAC TCT CGC ACT TAT CGT AAC GTT CGT TCT GCA GAA GAG        48
Met Ala Ser His Ser Arg Thr Tyr Arg Asn Val Arg Ser Ala Glu Glu
  1               5                  10                  15

CTG ATA TCT GAA ATA AAA AGG GAA TCA GAA ATT GGA AGG TTA CCT AAA        96
Leu Ile Ser Glu Ile Lys Arg Glu Ser Glu Ile Gly Arg Leu Pro Lys
             20                  25                  30

AGT GTT GCT TAT GCT ATG GAG GGA CTT TTT CAC TAC TAT CGC AAT GCA       144
Ser Val Ala Tyr Ala Met Glu Gly Leu Phe His Tyr Tyr Arg Asn Ala
         35                  40                  45

GTC CTT TCA AGT GGA ATT TCT CAT GCT GAT GAA ATA GTG TTG TCA AAC       192
Val Leu Ser Ser Gly Ile Ser His Ala Asp Glu Ile Val Leu Ser Asn
     50                  55                  60

ATG AGT GTT ATG CTT GAT TTT GTT TTG TTG GAT ATT GAG GAC CCT TTT       240
Met Ser Val Met Leu Asp Phe Val Leu Leu Asp Ile Glu Asp Pro Phe
 65                  70                  75                  80

GTA TTT CCA CCG TTT CAC AAA GCT ATT CGA GAG CCT GCT GAC TAT TAT       288
Val Phe Pro Pro Phe His Lys Ala Ile Arg Glu Pro Ala Asp Tyr Tyr
                 85                  90                  95
```

| | |
|---|---|
| TCC TTT GGT CAA GAT TAC ATT CGG CCA TTG GTA GAT TTT GGA AAT TCA<br>Ser Phe Gly Gln Asp Tyr Ile Arg Pro Leu Val Asp Phe Gly Asn Ser<br>                    100                            105                       110 | 336 |
| TAT GTT GGT AAC ATC GCC ATT TTC CAA GAA ATG GAG GAG AAG CTT AAG<br>Tyr Val Gly Asn Ile Ala Ile Phe Gln Glu Met Glu Glu Lys Leu Lys<br>                    115                            120                       125 | 384 |
| CAG GGT GAC AAC ATC ATC TTA ATG TCC AAC CAT CAA AGT GAA GCA GAT<br>Gln Gly Asp Asn Ile Ile Leu Met Ser Asn His Gln Ser Glu Ala Asp<br>130                              135                            140 | 432 |
| CCC GCA GTG ATT GCA TTA CTT CTG GAG AAG ACA AAT TCA CTA ATC GCA<br>Pro Ala Val Ile Ala Leu Leu Leu Glu Lys Thr Asn Ser Leu Ile Ala<br>145                              150                            155                       160 | 480 |
| GAA AAC TTG ATC TAC ATA GCA GGT GAT CGA GTT ATA ACA GAT CCT CTT<br>Glu Asn Leu Ile Tyr Ile Ala Gly Asp Arg Val Ile Thr Asp Pro Leu<br>                         165                            170                       175 | 528 |
| TGC AAG CCC TTT AGC ATG GGA AGG AAT CTT CTT TGT GTT TAC TCT AAG<br>Cys Lys Pro Phe Ser Met Gly Arg Asn Leu Leu Cys Val Tyr Ser Lys<br>                       180                            185                       190 | 576 |
| AAG CAC ATG TAT GAT GAT CCC GAG CTT GTT GAT GTA AAG AAA AGA GCA<br>Lys His Met Tyr Asp Asp Pro Glu Leu Val Asp Val Lys Lys Arg Ala<br>                    195                            200                       205 | 624 |
| AAT ACA AGG AGT TTG AAA GAG TTG GTC TTA CTT TTA AGA GGT GGT TCA<br>Asn Thr Arg Ser Leu Lys Glu Leu Val Leu Leu Leu Arg Gly Gly Ser<br>210                              215                            220 | 672 |
| AAA ATA ATC TGG ATT GCA CCC AGT GGT GGA AGA GAT CGT CCA GAT GCT<br>Lys Ile Ile Trp Ile Ala Pro Ser Gly Gly Arg Asp Arg Pro Asp Ala<br>225                              230                            235                     240 | 720 |
| GTC ACT GGT GAA TGG TAC CCA GCA CCC TTT GAT GCT TCT TCA GTG GAC<br>Val Thr Gly Glu Trp Tyr Pro Ala Pro Phe Asp Ala Ser Ser Val Asp<br>                       245                            250                       255 | 768 |
| AAC ATG AGA AGG CTT ATT CAA CAT TCG GAT GTT CCT GGG CAT TTG TTT<br>Asn Met Arg Arg Leu Ile Gln His Ser Asp Val Pro Gly His Leu Phe<br>                    260                            265                       270 | 816 |
| CCC CTT GCT TTA TTA TGT CAT GAC ATC ATG CCC CCT CCC TCA CAG GTC<br>Pro Leu Ala Leu Leu Cys His Asp Ile Met Pro Pro Pro Ser Gln Val<br>                    275                            280                       285 | 864 |
| GAA ATT GAA ATT GGA GAA AAA AGA GTG ATT GCC TTT AAT GGG GCG GGT<br>Glu Ile Glu Ile Gly Glu Lys Arg Val Ile Ala Phe Asn Gly Ala Gly<br>                    290                            295                       300 | 912 |
| TTG TCT GTG GCT CCT GAA ATC AGC TTC GAG GAA ATT GCT GCT ACC CAC<br>Leu Ser Val Ala Pro Glu Ile Ser Phe Glu Glu Ile Ala Ala Thr His<br>305                              310                            315                       320 | 960 |
| AAA AAT CCT GAG GAG GTT AGG GAG GCA TAC TCA AAG GCA CTG TTT GAT<br>Lys Asn Pro Glu Glu Val Arg Glu Ala Tyr Ser Lys Ala Leu Phe Asp<br>                           325                            330                       335 | 1008 |
| TCT GTG GCC ATG CAA TAC AAT GTG CTC AAA ACG GCT ATC TCC GGC AAA<br>Ser Val Ala Met Gln Tyr Asn Val Leu Lys Thr Ala Ile Ser Gly Lys<br>                    340                            345                       350 | 1056 |
| CAA GGA CTA GGA GCT TCA ACT GCG GAT GTC TCT TTG TCA CAA CCT TGG<br>Gln Gly Leu Gly Ala Ser Thr Ala Asp Val Ser Leu Ser Gln Pro Trp<br>                    355                            360                       365 | 1104 |

(2) INFORMATION FOR SEQ ID NO:2:

(i) SEQUENCE CHARACTERISTICS:
        (A) LENGTH: 368 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Ser His Ser Arg Thr Tyr Arg Asn Val Arg Ser Ala Glu Glu
 1               5                  10                  15

Leu Ile Ser Glu Ile Lys Arg Glu Ser Glu Ile Gly Arg Leu Pro Lys
              20                  25                  30

Ser Val Ala Tyr Ala Met Glu Gly Leu Phe His Tyr Tyr Arg Asn Ala
             35                  40                  45

Val Leu Ser Ser Gly Ile Ser His Ala Asp Glu Ile Val Leu Ser Asn
         50                  55                  60

Met Ser Val Met Leu Asp Phe Val Leu Leu Asp Ile Glu Asp Pro Phe
 65              70                  75                  80

Val Phe Pro Pro Phe His Lys Ala Ile Arg Glu Pro Ala Asp Tyr Tyr
                 85                  90                  95

Ser Phe Gly Gln Asp Tyr Ile Arg Pro Leu Val Asp Phe Gly Asn Ser
             100                 105                 110

Tyr Val Gly Asn Ile Ala Ile Phe Gln Glu Met Glu Lys Leu Lys
             115                 120                 125

Gln Gly Asp Asn Ile Ile Leu Met Ser Asn His Gln Ser Glu Ala Asp
 130                 135                 140

Pro Ala Val Ile Ala Leu Leu Leu Glu Lys Thr Asn Ser Leu Ile Ala
145                 150                 155                 160

Glu Asn Leu Ile Tyr Ile Ala Gly Asp Arg Val Ile Thr Asp Pro Leu
             165                 170                 175

Cys Lys Pro Phe Ser Met Gly Arg Asn Leu Leu Cys Val Tyr Ser Lys
             180                 185                 190

Lys His Met Tyr Asp Asp Pro Glu Leu Val Asp Val Lys Lys Arg Ala
             195                 200                 205

Asn Thr Arg Ser Leu Lys Glu Leu Val Leu Leu Arg Gly Gly Ser
 210                 215                 220

Lys Ile Ile Trp Ile Ala Pro Ser Gly Gly Arg Asp Arg Pro Asp Ala
225                 230                 235                 240

Val Thr Gly Glu Trp Tyr Pro Ala Pro Phe Asp Ala Ser Ser Val Asp
             245                 250                 255

Asn Met Arg Arg Leu Ile Gln His Ser Asp Val Pro Gly His Leu Phe
             260                 265                 270

Pro Leu Ala Leu Leu Cys His Asp Ile Met Pro Pro Ser Gln Val
             275                 280                 285

Glu Ile Glu Ile Gly Glu Lys Arg Val Ile Ala Phe Asn Gly Ala Gly
             290                 295                 300

Leu Ser Val Ala Pro Glu Ile Ser Phe Glu Glu Ile Ala Ala Thr His
305                 310                 315                 320

Lys Asn Pro Glu Glu Val Arg Glu Ala Tyr Ser Lys Ala Leu Phe Asp
                 325                 330                 335

Ser Val Ala Met Gln Tyr Asn Val Leu Lys Thr Ala Ile Ser Gly Lys
             340                 345                 350

Gln Gly Leu Gly Ala Ser Thr Ala Asp Val Ser Leu Ser Gln Pro Trp
             355                 360                 365

(2) INFORMATION FOR SEQ ID NO:3:

(i) SEQUENCE CHARACTERISTICS:
        (A) LENGTH: 1104 base pairs
        (B) TYPE: nucleic acid
        (C) STRANDEDNESS: double
        (D) TOPOLOGY: linear
```

(ii) MOLECULE TYPE: DNA (genomic)

(ix) FEATURE:
    (A) NAME/KEY: CDS
    (B) LOCATION: 1..1104

(xi) SEQUENCE DESCRIPTION: SEQ ID NO:3:

```
ATG GCT AGC CAC TCC CGC AAA TTT CTC GAT GTT CGC TCT GAA GAA GAG      48
Met Ala Ser His Ser Arg Lys Phe Leu Asp Val Arg Ser Glu Glu Glu
 1               5                  10                  15

TTG CTC TCC TGC ATC AAG AAG GAA ACA GAA GCT GGA AAG CTG CCT CCA      96
Leu Leu Ser Cys Ile Lys Lys Glu Thr Glu Ala Gly Lys Leu Pro Pro
                20                  25                  30

AAT GTT GCT GCA GGA ATG GAA GAA TTG TAT CAG AAT TAT AGA AAT GCT     144
Asn Val Ala Ala Gly Met Glu Glu Leu Tyr Gln Asn Tyr Arg Asn Ala
             35                  40                  45

GTT ATT GAG AGT GGA AAT CCA AAG GCA GAT GAA ATT GTT CTG TCT AAC     192
Val Ile Glu Ser Gly Asn Pro Lys Ala Asp Glu Ile Val Leu Ser Asn
         50                  55                  60

ATG ACT GTT GCA TTA GAT CGC ATA TTG TTG GAT GTG GAG GAT CCT TTT     240
Met Thr Val Ala Leu Asp Arg Ile Leu Leu Asp Val Glu Asp Pro Phe
 65                  70                  75                  80

GTC TTC TCA TCA CAC CAC AAA GCA ATT CGA GAG CCT TTT GAT TAC TAC     288
Val Phe Ser Ser His His Lys Ala Ile Arg Glu Pro Phe Asp Tyr Tyr
                 85                  90                  95

ATT TTT GGC CAG AAC TAT ATA CGG CCA TTG ATT GAT TTT GGA AAT TCA     336
Ile Phe Gly Gln Asn Tyr Ile Arg Pro Leu Ile Asp Phe Gly Asn Ser
            100                 105                 110

TTC GTT GGT AAC CTT TCT CTT TTC AAG GAT ATA GAA GAG AAG CTT AAG     384
Phe Val Gly Asn Leu Ser Leu Phe Lys Asp Ile Glu Glu Lys Leu Lys
        115                 120                 125

CAG GGT GAC AAC ATC ATC TTA ATG TCC AAC CAT CAA AGT GAA GCA GAT     432
Gln Gly Asp Asn Ile Ile Leu Met Ser Asn His Gln Ser Glu Ala Asp
    130                 135                 140

CCC GCA GTG ATT GCA TTA CTT CTG GAG AAG ACA AAT TCA CTA ATC GCA     480
Pro Ala Val Ile Ala Leu Leu Leu Glu Lys Thr Asn Ser Leu Ile Ala
145                 150                 155                 160

GAA AAC TTG ATC TAC ATA GCA GGT GAT CGA GTT ATA ACA GAT CCT CTT     528
Glu Asn Leu Ile Tyr Ile Ala Gly Asp Arg Val Ile Thr Asp Pro Leu
                165                 170                 175

TGC AAG CCC TTT AGC ATG GGA AGG AAT CTT CTT TGT GTT TAC TCT AAG     576
Cys Lys Pro Phe Ser Met Gly Arg Asn Leu Leu Cys Val Tyr Ser Lys
            180                 185                 190

AAG CAC ATG TAT GAT GAT CCC GAG CTT GTT GAT GTA AAG AAA AGA GCA     624
Lys His Met Tyr Asp Asp Pro Glu Leu Val Asp Val Lys Lys Arg Ala
        195                 200                 205

AAT ACA AGG AGT TTG AAA GAG TTG GTC TTA CTT TTA AGA GGT GGT TCA     672
Asn Thr Arg Ser Leu Lys Glu Leu Val Leu Leu Leu Arg Gly Gly Ser
    210                 215                 220

AAA ATA ATC TGG ATT GCA CCC AGT GGT GGA AGA GAT CGT CCA GAT GCT     720
Lys Ile Ile Trp Ile Ala Pro Ser Gly Gly Arg Asp Arg Pro Asp Ala
225                 230                 235                 240

GTC ACT GGT GAA TGG TAC CCA GCA CCC TTT GAT GCT TCT TCA GTG GAC     768
Val Thr Gly Glu Trp Tyr Pro Ala Pro Phe Asp Ala Ser Ser Val Asp
                245                 250                 255

AAC ATG AGA AGG CTT ATT CAA CAT TCG GAT GTT CCT GGG CAT TTG TTT     816
Asn Met Arg Arg Leu Ile Gln His Ser Asp Val Pro Gly His Leu Phe
            260                 265                 270

CCC CTT GCT TTA TTA TGT CAT GAC ATC ATG CCC CCT CCC TCA CAG GTC     864
Pro Leu Ala Leu Leu Cys His Asp Ile Met Pro Pro Pro Ser Gln Val
        275                 280                 285
```

```
GAA ATT GAA ATT GGA GAA AAA AGA GTG ATT GCC TTT AAT GGG GCG GGT      912
Glu Ile Glu Ile Gly Glu Lys Arg Val Ile Ala Phe Asn Gly Ala Gly
            290                 295                 300

TTG TCT GTG GCT CCT GAA ATC AGC TTC GAG GAA ATT GCT GCT ACC CAC      960
Leu Ser Val Ala Pro Glu Ile Ser Phe Glu Glu Ile Ala Ala Thr His
305                 310                 315                 320

AAA AAT CCT GAG GAG GTT AGG GAG GCA TAC TCA AAG GCA CTG TTT GAT     1008
Lys Asn Pro Glu Glu Val Arg Glu Ala Tyr Ser Lys Ala Leu Phe Asp
                325                 330                 335

TCT GTG GCC ATG CAA TAC AAT GTG CTC AAA ACG GCT ATC TCC GGC AAA     1056
Ser Val Ala Met Gln Tyr Asn Val Leu Lys Thr Ala Ile Ser Gly Lys
            340                 345                 350

CAA GGA CTA GGA GCT TCA ACT GCG GAT GTC TCT TTG TCA CAA CCT TGG     1104
Gln Gly Leu Gly Ala Ser Thr Ala Asp Val Ser Leu Ser Gln Pro Trp
                355                 360                 365

(2) INFORMATION FOR SEQ ID NO:4:

(i) SEQUENCE CHARACTERISTICS:
        (A) LENGTH: 368 amino acids
        (B) TYPE: amino acid
        (D) TOPOLOGY: linear (ii) MOLECULE TYPE: protein (xi) SEQUENCE DESCRIPTION: SEQ ID NO:4:

Met Ala Ser His Ser Arg Lys Phe Leu Asp Val Arg Ser Glu Glu Glu
1               5                   10                  15

Leu Leu Ser Cys Ile Lys Lys Glu Thr Glu Ala Gly Lys Leu Pro Pro
                20                  25                  30

Asn Val Ala Ala Gly Met Glu Glu Leu Tyr Gln Asn Tyr Arg Asn Ala
            35                  40                  45

Val Ile Glu Ser Gly Asn Pro Lys Ala Asp Glu Ile Val Leu Ser Asn
        50                  55                  60

Met Thr Val Ala Leu Asp Arg Ile Leu Leu Asp Val Glu Asp Pro Phe
65                  70                  75                  80

Val Phe Ser Ser His His Lys Ala Ile Arg Glu Pro Phe Asp Tyr Tyr
                85                  90                  95

Ile Phe Gly Gln Asn Tyr Ile Arg Pro Leu Ile Asp Phe Gly Asn Ser
                100                 105                 110

Phe Val Gly Asn Leu Ser Leu Phe Lys Asp Ile Glu Glu Lys Leu Lys
            115                 120                 125

Gln Gly Asp Asn Ile Ile Leu Met Ser Asn His Gln Ser Glu Ala Asp
130                 135                 140

Pro Ala Val Ile Ala Leu Leu Leu Glu Lys Thr Asn Ser Leu Ile Ala
145                 150                 155                 160

Glu Asn Leu Ile Tyr Ile Ala Gly Asp Arg Val Ile Thr Asp Pro Leu
                165                 170                 175

Cys Lys Pro Phe Ser Met Gly Arg Asn Leu Leu Cys Val Tyr Ser Lys
            180                 185                 190

Lys His Met Tyr Asp Asp Pro Glu Leu Val Asp Val Lys Lys Arg Ala
        195                 200                 205

Asn Thr Arg Ser Leu Lys Glu Leu Val Leu Leu Arg Gly Gly Ser
            210                 215                 220

Lys Ile Ile Trp Ile Ala Pro Ser Gly Gly Arg Asp Arg Pro Asp Ala
225                 230                 235                 240

Val Thr Gly Glu Trp Tyr Pro Ala Pro Phe Asp Ala Ser Ser Val Asp
```

```
                  245                 250                 255
Asn Met Arg Arg Leu Ile Gln His Ser Asp Val Pro Gly His Leu Phe
            260                 265                 270

Pro Leu Ala Leu Leu Cys His Asp Ile Met Pro Pro Ser Gln Val
        275                 280                 285

Glu Ile Glu Ile Gly Glu Lys Arg Val Ile Ala Phe Asn Gly Ala Gly
        290                 295                 300

Leu Ser Val Ala Pro Glu Ile Ser Phe Glu Glu Ile Ala Ala Thr His
305                 310                 315                 320

Lys Asn Pro Glu Glu Val Arg Glu Ala Tyr Ser Lys Ala Leu Phe Asp
                325                 330                 335

Ser Val Ala Met Gln Tyr Asn Val Leu Lys Thr Ala Ile Ser Gly Lys
            340                 345                 350

Gln Gly Leu Gly Ala Ser Thr Ala Asp Val Ser Leu Ser Gln Pro Trp
        355                 360                 365
```

(2) INFORMATION FOR SEQ ID NO:5:

(i) SEQUENCE CHARACTERISTICS:
        (A) LENGTH: 1104 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..1104

(xi) SEQUENCE DESCRIPTION: SEQ ID NO:5:

```
ATG GCT AGC CAC TCC CGC AAA TTT CTC GAT GTT CGC TCT GAA GAA GAG       48
Met Ala Ser His Ser Arg Lys Phe Leu Asp Val Arg Ser Glu Glu Glu
1               5                   10                  15

TTG CTC TCC TGC ATC AAG AAG GAA ACA GAA GCT GGA AAG CTG CCT CCA       96
Leu Leu Ser Cys Ile Lys Lys Glu Thr Glu Ala Gly Lys Leu Pro Pro
                20                  25                  30

AAT GTT GCT GCA GGA ATG GAA GAA TTG TAT CAG AAT TAT AGA AAT GCT      144
Asn Val Ala Ala Gly Met Glu Glu Leu Tyr Gln Asn Tyr Arg Asn Ala
            35                  40                  45

GTT ATT GAG AGT GGA AAT CCA AAG GCA GAT GAA ATT GTT CTG TCT AAC      192
Val Ile Glu Ser Gly Asn Pro Lys Ala Asp Glu Ile Val Leu Ser Asn
        50                  55                  60

ATG ACT GTT GCA TTA GAT CGC ATA TTG TTG GAT GTG GAG GAT CCT TTT      240
Met Thr Val Ala Leu Asp Arg Ile Leu Leu Asp Val Glu Asp Pro Phe
65                  70                  75                  80

GTC TTC TCA TCA CAC CAC AAA GCA ATT CGA GAG CCT TTT GAT TAC TAC      288
Val Phe Ser Ser His His Lys Ala Ile Arg Glu Pro Phe Asp Tyr Tyr
                85                  90                  95

ATT TTT GGC CAG AAC TAT ATA CGG CCA TTG ATT GAT TTT GGA AAT TCA      336
Ile Phe Gly Gln Asn Tyr Ile Arg Pro Leu Ile Asp Phe Gly Asn Ser
                100                 105                 110

TTC GTT GGT AAC CTT TCT CTT TTC AAG GAT ATA GAA GAG AAG CTT AAG      384
Phe Val Gly Asn Leu Ser Leu Phe Lys Asp Ile Glu Glu Lys Leu Lys
            115                 120                 125

CAG GGT GAC AAC ATC ATC TTA ATG TCC AAC CAT CAA AGT GAA GCA GAT      432
Gln Gly Asp Asn Ile Ile Leu Met Ser Asn His Gln Ser Glu Ala Asp
        130                 135                 140

CCC GCA GTG ATT GCA TTA CTT CTG GAG AAG ACA AAT TCA CTA ATC GCA      480
Pro Ala Val Ile Ala Leu Leu Leu Glu Lys Thr Asn Ser Leu Ile Ala
145                 150                 155                 160
```

```
GAA AAC TTG ATC TAC ATA GCA GGT GAT CGA GTT ATA ACA GAT CCT CTT      528
Glu Asn Leu Ile Tyr Ile Ala Gly Asp Arg Val Ile Thr Asp Pro Leu
            165                 170                 175

TGC AAG CCC TTT AGC ATG GGA AGG AAT CTT CTT TGT GTT TAC TCT AAG      576
Cys Lys Pro Phe Ser Met Gly Arg Asn Leu Leu Cys Val Tyr Ser Lys
            180                 185                 190

AAG CAC ATG TAT GAT GAT CCC GAG CTC ACA GAA ACA AAA AGG AAA GCA      624
Lys His Met Tyr Asp Asp Pro Glu Leu Thr Glu Thr Lys Arg Lys Ala
            195                 200                 205

AAC ACA CGA AGT CTT AAG GAG ATG GCT TTA CTC TTA AGA GGT GGA TCA      672
Asn Thr Arg Ser Leu Lys Glu Met Ala Leu Leu Leu Arg Gly Gly Ser
    210                 215                 220

CAA CTA ATA TGG ATT GCA CCC AGT GGT GGT AGG GAC CGG CCG GAT CCC      720
Gln Leu Ile Trp Ile Ala Pro Ser Gly Gly Arg Asp Arg Pro Asp Pro
225                 230                 235                 240

TCG ACT GGA GAA TGG TAC CCA GCA CCC TTT GAT GCT TCT TCA GTG GAC      768
Ser Thr Gly Glu Trp Tyr Pro Ala Pro Phe Asp Ala Ser Ser Val Asp
            245                 250                 255

AAC ATG AGA AGG CTT ATT CAA CAT TCG GAT GTT CCT GGG CAT TTG TTT      816
Asn Met Arg Arg Leu Ile Gln His Ser Asp Val Pro Gly His Leu Phe
            260                 265                 270

CCC CTT GCT TTA TTA TGT CAT GAC ATC ATG CCC CCT CCC TCA CAG GTC      864
Pro Leu Ala Leu Leu Cys His Asp Ile Met Pro Pro Pro Ser Gln Val
            275                 280                 285

GAA ATT GAA ATT GGA GAA AAA AGA GTG ATT GCC TTT AAT GGG GCG GGT      912
Glu Ile Glu Ile Gly Glu Lys Arg Val Ile Ala Phe Asn Gly Ala Gly
        290                 295                 300

TTG TCT GTG GCT CCT GAA ATC AGC TTC GAG GAA ATT GCT GCT ACC CAC      960
Leu Ser Val Ala Pro Glu Ile Ser Phe Glu Glu Ile Ala Ala Thr His
305                 310                 315                 320

AAA AAT CCT GAG GAG GTT AGG GAG GCA TAC TCA AAG GCA CTG TTT GAT     1008
Lys Asn Pro Glu Glu Val Arg Glu Ala Tyr Ser Lys Ala Leu Phe Asp
                325                 330                 335

TCT GTG GCC ATG CAA TAC AAT GTG CTC AAA ACG GCT ATC TCC GGC AAA     1056
Ser Val Ala Met Gln Tyr Asn Val Leu Lys Thr Ala Ile Ser Gly Lys
            340                 345                 350

CAA GGA CTA GGA GCT TCA ACT GCG GAT GTC TCT TTG TCA CAA CCT TGG     1104
Gln Gly Leu Gly Ala Ser Thr Ala Asp Val Ser Leu Ser Gln Pro Trp
            355                 360                 365
```

(2) INFORMATION FOR SEQ ID NO:6:

(i) SEQUENCE CHARACTERISTICS:
        (A) LENGTH: 368 amino acids
        (B) TYPE: amino acid
        (D) TOPOLOGY: linear (ii) MOLECULE TYPE: protein (xi) SEQUENCE DESCRIPTION: SEQ ID NO:6:

```
Met Ala Ser His Ser Arg Lys Phe Leu Asp Val Arg Ser Glu Glu Glu
1               5                   10                  15

Leu Leu Ser Cys Ile Lys Lys Glu Thr Glu Ala Gly Lys Leu Pro Pro
                20                  25                  30

Asn Val Ala Ala Gly Met Glu Glu Leu Tyr Gln Asn Tyr Arg Asn Ala
            35                  40                  45

Val Ile Glu Ser Gly Asn Pro Lys Ala Asp Glu Ile Val Leu Ser Asn
        50                  55                  60

Met Thr Val Ala Leu Asp Arg Ile Leu Leu Asp Val Glu Asp Pro Phe
65                  70                  75                  80
```

```
Val Phe Ser Ser His His Lys Ala Ile Arg Glu Pro Phe Asp Tyr Tyr
                85                  90                  95

Ile Phe Gly Gln Asn Tyr Ile Arg Pro Leu Ile Asp Phe Gly Asn Ser
            100                 105                 110

Phe Val Gly Asn Leu Ser Leu Phe Lys Asp Ile Glu Glu Lys Leu Lys
        115                 120                 125

Gln Gly Asp Asn Ile Ile Leu Met Ser Asn His Gln Ser Glu Ala Asp
    130                 135                 140

Pro Ala Val Ile Ala Leu Leu Glu Lys Thr Asn Ser Leu Ile Ala
145                 150                 155                 160

Glu Asn Leu Ile Tyr Ile Ala Gly Asp Arg Val Ile Thr Asp Pro Leu
                165                 170                 175

Cys Lys Pro Phe Ser Met Gly Arg Asn Leu Leu Cys Val Tyr Ser Lys
            180                 185                 190

Lys His Met Tyr Asp Asp Pro Glu Leu Thr Glu Thr Lys Arg Lys Ala
        195                 200                 205

Asn Thr Arg Ser Leu Lys Glu Met Ala Leu Leu Arg Gly Gly Ser
    210                 215                 220

Gln Leu Ile Trp Ile Ala Pro Ser Gly Gly Arg Asp Arg Pro Asp Pro
225                 230                 235                 240

Ser Thr Gly Glu Trp Tyr Pro Ala Pro Phe Asp Ala Ser Ser Val Asp
                245                 250                 255

Asn Met Arg Arg Leu Ile Gln His Ser Asp Val Pro Gly His Leu Phe
            260                 265                 270

Pro Leu Ala Leu Leu Cys His Asp Ile Met Pro Pro Ser Gln Val
    275                 280                 285

Glu Ile Glu Ile Gly Glu Lys Arg Val Ile Ala Phe Asn Gly Ala Gly
290                 295                 300

Leu Ser Val Ala Pro Glu Ile Ser Phe Glu Glu Ile Ala Ala Thr His
305                 310                 315                 320

Lys Asn Pro Glu Glu Val Arg Glu Ala Tyr Ser Lys Ala Leu Phe Asp
                325                 330                 335

Ser Val Ala Met Gln Tyr Asn Val Leu Lys Thr Ala Ile Ser Gly Lys
            340                 345                 350

Gln Gly Leu Gly Ala Ser Thr Ala Asp Val Ser Leu Ser Gln Pro Trp
        355                 360                 365

(2) INFORMATION FOR SEQ ID NO:7:

(i) SEQUENCE CHARACTERISTICS:
        (A) LENGTH: 1104 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..1104

(xi) SEQUENCE DESCRIPTION: SEQ ID NO:7:

CAA CTT CTT CGT TCT CGC ACT TAT CGT AAC GTT CGT TCT GCA GAA GAG      48
Gln Leu Leu Arg Ser Arg Thr Tyr Arg Asn Val Arg Ser Ala Glu Glu
  1               5                  10                  15

CTG ATA TCT GAA ATA AAA AGG GAA TCA GAA ATT GGA AGG TTA CCT AAA      96
Leu Ile Ser Glu Ile Lys Arg Glu Ser Glu Ile Gly Arg Leu Pro Lys
            20                  25                  30
```

```
AGT GTT GCT TAT GCT ATG GAG GGA CTT TTT CAC TAC TAT CGC AAT GCA        144
Ser Val Ala Tyr Ala Met Glu Gly Leu Phe His Tyr Tyr Arg Asn Ala
         35                  40                  45

GTC CTT TCA AGT GGA ATT TCT CAT GCT GAT GAA ATA GTG TTG TCA AAC        192
Val Leu Ser Ser Gly Ile Ser His Ala Asp Glu Ile Val Leu Ser Asn
 50                  55                  60

ATG AGT GTT ATG CTT GAT TTT GTT TTG TTG GAT ATT GAG GAC CCT TTT        240
Met Ser Val Met Leu Asp Phe Val Leu Leu Asp Ile Glu Asp Pro Phe
 65                  70                  75                  80

GTA TTT CCA CCG TTT CAC AAA GCT ATT CGA GAG CCT GCT GAC TAT TAT        288
Val Phe Pro Pro Phe His Lys Ala Ile Arg Glu Pro Ala Asp Tyr Tyr
                 85                  90                  95

TCC TTT GGT CAA GAT TAC ATT CGG CCA TTG GTA GAT TTT GGA AAT TCA        336
Ser Phe Gly Gln Asp Tyr Ile Arg Pro Leu Val Asp Phe Gly Asn Ser
            100                 105                 110

TAT GTT GGT AAC ATC GCC ATT TTC CAA GAA ATG GAG GAG AAG CTT AAG        384
Tyr Val Gly Asn Ile Ala Ile Phe Gln Glu Met Glu Glu Lys Leu Lys
        115                 120                 125

CAG GGT GAC AAC ATC ATC TTA ATG TCC AAC CAT CAA AGT GAA GCA GAT        432
Gln Gly Asp Asn Ile Ile Leu Met Ser Asn His Gln Ser Glu Ala Asp
130                 135                 140

CCC GCA GTG ATT GCA TTA CTT CTG GAG AAG ACA AAT TCA CTA ATC GCA        480
Pro Ala Val Ile Ala Leu Leu Leu Glu Lys Thr Asn Ser Leu Ile Ala
145                 150                 155                 160

GAA AAC TTG ATC TAC ATA GCA GGT GAT CGA GTT ATA ACA GAT CCT CTT        528
Glu Asn Leu Ile Tyr Ile Ala Gly Asp Arg Val Ile Thr Asp Pro Leu
                165                 170                 175

TGC AAG CCC TTT AGC ATG GGA AGG AAT CTT CTT TGT GTT TAC TCT AAG        576
Cys Lys Pro Phe Ser Met Gly Arg Asn Leu Leu Cys Val Tyr Ser Lys
            180                 185                 190

AAG CAC ATG TAT GAT GAT CCC GAG CTT GTT GAT GTA AAG AAA AGA GCA        624
Lys His Met Tyr Asp Asp Pro Glu Leu Val Asp Val Lys Lys Arg Ala
        195                 200                 205

AAT ACA AGG AGT TTG AAA GAG TTG GTC TTA CTT TTA AGA GGT GGT TCA        672
Asn Thr Arg Ser Leu Lys Glu Leu Val Leu Leu Leu Arg Gly Gly Ser
210                 215                 220

AAA ATA ATC TGG ATT GCA CCC AGT GGT GGA AGA GAT CGT CCA GAT GCT        720
Lys Ile Ile Trp Ile Ala Pro Ser Gly Gly Arg Asp Arg Pro Asp Ala
225                 230                 235                 240

GTC ACT GGT GAA TGG TAC CCA GCA CCC TTT GAT GCT TCT TCA GTG GAC        768
Val Thr Gly Glu Trp Tyr Pro Ala Pro Phe Asp Ala Ser Ser Val Asp
                245                 250                 255

AAC ATG AGA AGG CTT ATT CAA CAT TCG GAT GTT CCT GGG CAT TTG TTT        816
Asn Met Arg Arg Leu Ile Gln His Ser Asp Val Pro Gly His Leu Phe
            260                 265                 270

CCC CTT GCT TTA TTA TGT CAT GAC ATC ATG CCC CCT CCC TCA CAG GTC        864
Pro Leu Ala Leu Leu Cys His Asp Ile Met Pro Pro Pro Ser Gln Val
        275                 280                 285

GAA ATT GAA ATT GGA GAA AAA AGA GTG ATT GCC TTT AAT GGG GCG GGT        912
Glu Ile Glu Ile Gly Glu Lys Arg Val Ile Ala Phe Asn Gly Ala Gly
290                 295                 300

TTG TCT GTG GCT CCT GAA ATC AGC TTC GAG GAA ATT GCT GCT ACC CAC        960
Leu Ser Val Ala Pro Glu Ile Ser Phe Glu Glu Ile Ala Ala Thr His
305                 310                 315                 320

AAA AAT CCT GAG GAG GTT AGG GAG GCA TAC TCA AAG GCA CTG TTT GAT       1008
Lys Asn Pro Glu Glu Val Arg Glu Ala Tyr Ser Lys Ala Leu Phe Asp
                325                 330                 335

TCT GTG GCC ATG CAA TAC AAT GTG CTC AAA ACG GCT ATC TCC GGC AAA       1056
Ser Val Ala Met Gln Tyr Asn Val Leu Lys Thr Ala Ile Ser Gly Lys
```

-continued

```
                340                  345                  350
CAA GGA CTA GGA GCT TCA ACT GCG GAT GTC TCT TTG TCA CAA CCT TGG    1104
Gln Gly Leu Gly Ala Ser Thr Ala Asp Val Ser Leu Ser Gln Pro Trp
        355                  360                  365
```

(2) INFORMATION FOR SEQ ID NO:8:

(i) SEQUENCE CHARACTERISTICS:
        (A) LENGTH: 368 amino acids
        (B) TYPE: amino acid
        (D) TOPOLOGY: linear (ii) MOLECULE TYPE: protein (xi) SEQUENCE DESCRIPTION: SEQ ID NO:8:

```
Gln Leu Leu Arg Ser Arg Thr Tyr Arg Asn Val Arg Ser Ala Glu Glu
  1               5                  10                  15

Leu Ile Ser Glu Ile Lys Arg Glu Ser Glu Ile Gly Arg Leu Pro Lys
             20                  25                  30

Ser Val Ala Tyr Ala Met Glu Gly Leu Phe His Tyr Tyr Arg Asn Ala
         35                  40                  45

Val Leu Ser Ser Gly Ile Ser His Ala Asp Glu Ile Val Leu Ser Asn
     50                  55                  60

Met Ser Val Met Leu Asp Phe Val Leu Leu Asp Ile Glu Asp Pro Phe
 65                  70                  75                  80

Val Phe Pro Pro Phe His Lys Ala Ile Arg Glu Pro Ala Asp Tyr Tyr
                 85                  90                  95

Ser Phe Gly Gln Asp Tyr Ile Arg Pro Leu Val Asp Phe Gly Asn Ser
            100                 105                 110

Tyr Val Gly Asn Ile Ala Ile Phe Gln Glu Met Glu Glu Lys Leu Lys
        115                 120                 125

Gln Gly Asp Asn Ile Ile Leu Met Ser Asn His Gln Ser Glu Ala Asp
    130                 135                 140

Pro Ala Val Ile Ala Leu Leu Leu Glu Lys Thr Asn Ser Leu Ile Ala
145                 150                 155                 160

Glu Asn Leu Ile Tyr Ile Ala Gly Asp Arg Val Ile Thr Asp Pro Leu
                165                 170                 175

Cys Lys Pro Phe Ser Met Gly Arg Asn Leu Leu Cys Val Tyr Ser Lys
            180                 185                 190

Lys His Met Tyr Asp Asp Pro Glu Leu Val Asp Val Lys Lys Arg Ala
        195                 200                 205

Asn Thr Arg Ser Leu Lys Glu Leu Val Leu Leu Arg Gly Gly Ser
    210                 215                 220

Lys Ile Ile Trp Ile Ala Pro Ser Gly Gly Arg Asp Arg Pro Asp Ala
225                 230                 235                 240

Val Thr Gly Glu Trp Tyr Pro Ala Pro Phe Asp Ala Ser Ser Val Asp
                245                 250                 255

Asn Met Arg Arg Leu Ile Gln His Ser Asp Val Pro Gly His Leu Phe
            260                 265                 270

Pro Leu Ala Leu Leu Cys His Asp Ile Met Pro Pro Ser Gln Val
        275                 280                 285

Glu Ile Glu Ile Gly Glu Lys Arg Val Ile Ala Phe Asn Gly Ala Gly
    290                 295                 300

Leu Ser Val Ala Pro Glu Ile Ser Phe Glu Glu Ile Ala Ala Thr His
305                 310                 315                 320

Lys Asn Pro Glu Glu Val Arg Glu Ala Tyr Ser Lys Ala Leu Phe Asp
```

```
                   325                 330                 335
Ser Val Ala Met Gln Tyr Asn Val Leu Lys Thr Ala Ile Ser Gly Lys
                       340                 345                 350
Gln Gly Leu Gly Ala Ser Thr Ala Asp Val Ser Leu Ser Gln Pro Trp
        355                 360                 365
```

(2) INFORMATION FOR SEQ ID NO:9:

(i) SEQUENCE CHARACTERISTICS:
        (A) LENGTH: 1104 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..1104

(xi) SEQUENCE DESCRIPTION: SEQ ID NO:9:

```
GAG CCG GCT CAC TCC CGC AAA TTT CTC GAT GTT CGC TCT GAA GAA GAG        48
Glu Pro Ala His Ser Arg Lys Phe Leu Asp Val Arg Ser Glu Glu Glu
 1               5                  10                  15

TTG CTC TCC TGC ATC AAG AAG GAA ACA GAA GCT GGA AAG CTG CCT CCA        96
Leu Leu Ser Cys Ile Lys Lys Glu Thr Glu Ala Gly Lys Leu Pro Pro
                20                  25                  30

AAT GTT GCT GCA GGA ATG GAA GAA TTG TAT CAG AAT TAT AGA AAT GCT       144
Asn Val Ala Ala Gly Met Glu Glu Leu Tyr Gln Asn Tyr Arg Asn Ala
            35                  40                  45

GTT ATT GAG AGT GGA AAT CCA AAG GCA GAT GAA ATT GTT CTG TCT AAC       192
Val Ile Glu Ser Gly Asn Pro Lys Ala Asp Glu Ile Val Leu Ser Asn
         50                  55                  60

ATG ACT GTT GCA TTA GAT CGC ATA TTG TTG GAT GTG GAG GAT CCT TTT       240
Met Thr Val Ala Leu Asp Arg Ile Leu Leu Asp Val Glu Asp Pro Phe
 65                  70                  75                  80

GTC TTC TCA TCA CAC CAC AAA GCA ATT CGA GAG CCT TTT GAT TAC TAC       288
Val Phe Ser Ser His His Lys Ala Ile Arg Glu Pro Phe Asp Tyr Tyr
                 85                  90                  95

ATT TTT GGC CAG AAC TAT ATA CGG CCA TTG ATT GAT TTT GGA AAT TCA       336
Ile Phe Gly Gln Asn Tyr Ile Arg Pro Leu Ile Asp Phe Gly Asn Ser
            100                 105                 110

TTC GTT GGT AAC CTT TCT CTT TTC AAG GAT ATA GAA GAG AAG CTT AAG       384
Phe Val Gly Asn Leu Ser Leu Phe Lys Asp Ile Glu Glu Lys Leu Lys
        115                 120                 125

CAG GGT GAC AAC ATC ATC TTA ATG TCC AAC CAT CAA AGT GAA GCA GAT       432
Gln Gly Asp Asn Ile Ile Leu Met Ser Asn His Gln Ser Glu Ala Asp
    130                 135                 140

CCC GCA GTG ATT GCA TTA CTT CTG GAG AAG ACA AAT TCA CTA ATC GCA       480
Pro Ala Val Ile Ala Leu Leu Leu Glu Lys Thr Asn Ser Leu Ile Ala
145                 150                 155                 160

GAA AAC TTG ATC TAC ATA GCA GGT GAT CGA GTT ATA ACA GAT CCT CTT       528
Glu Asn Leu Ile Tyr Ile Ala Gly Asp Arg Val Ile Thr Asp Pro Leu
                165                 170                 175

TGC AAG CCC TTT AGC ATG GGA AGG AAT CTT CTT TGT GTT TAC TCT AAG       576
Cys Lys Pro Phe Ser Met Gly Arg Asn Leu Leu Cys Val Tyr Ser Lys
            180                 185                 190

AAG CAC ATG TAT GAT GAT CCC GAG CTT GTT GAT GTA AAG AAA AGA GCA       624
Lys His Met Tyr Asp Asp Pro Glu Leu Val Asp Val Lys Lys Arg Ala
        195                 200                 205

AAT ACA AGG AGT TTG AAA GAG TTG GTC TTA CTT TTA AGA GGT GGT TCA       672
Asn Thr Arg Ser Leu Lys Glu Leu Val Leu Leu Leu Arg Gly Gly Ser
    210                 215                 220
```

```
                210                 215                 220
AAA ATA ATC TGG ATT GCA CCC AGT GGT GGA AGA GAT CGT CCA GAT GCT       720
Lys Ile Ile Trp Ile Ala Pro Ser Gly Gly Arg Asp Arg Pro Asp Ala
225                 230                 235                 240

GTC ACT GGT GAA TGG TAC CCA GCA CCC TTT GAT GCT TCT TCA GTG GAC       768
Val Thr Gly Glu Trp Tyr Pro Ala Pro Phe Asp Ala Ser Ser Val Asp
                245                 250                 255

AAC ATG AGA AGG CTT ATT CAA CAT TCG GAT GTT CCT GGG CAT TTG TTT       816
Asn Met Arg Arg Leu Ile Gln His Ser Asp Val Pro Gly His Leu Phe
            260                 265                 270

CCC CTT GCT TTA TTA TGT CAT GAC ATC ATG CCC CCT CCC TCA CAG GTC       864
Pro Leu Ala Leu Leu Cys His Asp Ile Met Pro Pro Pro Ser Gln Val
        275                 280                 285

GAA ATT GAA ATT GGA GAA AAA AGA GTG ATT GCC TTT AAT GGG GCG GGT       912
Glu Ile Glu Ile Gly Glu Lys Arg Val Ile Ala Phe Asn Gly Ala Gly
290                 295                 300

TTG TCT GTG GCT CCT GAA ATC AGC TTC GAG GAA ATT GCT GCT ACC CAC       960
Leu Ser Val Ala Pro Glu Ile Ser Phe Glu Glu Ile Ala Ala Thr His
305                 310                 315                 320

AAA AAT CCT GAG GAG GTT AGG GAG GCA TAC TCA AAG GCA CTG TTT GAT      1008
Lys Asn Pro Glu Glu Val Arg Glu Ala Tyr Ser Lys Ala Leu Phe Asp
                325                 330                 335

TCT GTG GCC ATG CAA TAC AAT GTG CTC AAA ACG GCT ATC TCC GGC AAA      1056
Ser Val Ala Met Gln Tyr Asn Val Leu Lys Thr Ala Ile Ser Gly Lys
            340                 345                 350

CAA GGA CTA GGA GCT TCA ACT GCG GAT GTC TCT TTG TCA CAA CCT TGG      1104
Gln Gly Leu Gly Ala Ser Thr Ala Asp Val Ser Leu Ser Gln Pro Trp
        355                 360                 365

(2) INFORMATION FOR SEQ ID NO:10:

(i) SEQUENCE CHARACTERISTICS:
        (A) LENGTH: 368 amino acids
        (B) TYPE: amino acid
        (D) TOPOLOGY: linear (ii) MOLECULE TYPE: protein (xi) SEQUENCE DESCRIPTION: SEQ ID NO:10:

Glu Pro Ala His Ser Arg Lys Phe Leu Asp Val Arg Ser Glu Glu
1               5                   10                  15

Leu Leu Ser Cys Ile Lys Lys Glu Thr Glu Ala Gly Lys Leu Pro Pro
            20                  25                  30

Asn Val Ala Ala Gly Met Glu Glu Leu Tyr Gln Asn Tyr Arg Asn Ala
        35                  40                  45

Val Ile Glu Ser Gly Asn Pro Lys Ala Asp Glu Ile Val Leu Ser Asn
    50                  55                  60

Met Thr Val Ala Leu Asp Arg Ile Leu Leu Asp Val Glu Asp Pro Phe
65                  70                  75                  80

Val Phe Ser Ser His His Lys Ala Ile Arg Glu Pro Phe Asp Tyr Tyr
                85                  90                  95

Ile Phe Gly Gln Asn Tyr Ile Arg Pro Leu Ile Asp Phe Gly Asn Ser
            100                 105                 110

Phe Val Gly Asn Leu Ser Leu Phe Lys Asp Ile Glu Glu Lys Leu Lys
        115                 120                 125

Gln Gly Asp Asn Ile Ile Leu Met Ser Asn His Gln Ser Glu Ala Asp
    130                 135                 140

Pro Ala Val Ile Ala Leu Leu Glu Lys Thr Asn Ser Leu Ile Ala
145                 150                 155                 160
```

```
Glu Asn Leu Ile Tyr Ile Ala Gly Asp Arg Val Ile Thr Asp Pro Leu
                165                 170                 175

Cys Lys Pro Phe Ser Met Gly Arg Asn Leu Leu Cys Val Tyr Ser Lys
            180                 185                 190

Lys His Met Tyr Asp Asp Pro Glu Leu Val Asp Val Lys Lys Arg Ala
        195                 200                 205

Asn Thr Arg Ser Leu Lys Glu Leu Val Leu Leu Arg Gly Gly Ser
    210                 215                 220

Lys Ile Ile Trp Ile Ala Pro Ser Gly Arg Asp Arg Pro Asp Ala
225             230                 235                 240

Val Thr Gly Glu Trp Tyr Pro Ala Pro Phe Asp Ala Ser Ser Val Asp
            245                 250                 255

Asn Met Arg Arg Leu Ile Gln His Ser Asp Val Pro Gly His Leu Phe
            260                 265                 270

Pro Leu Ala Leu Leu Cys His Asp Ile Met Pro Pro Ser Gln Val
    275                 280                 285

Glu Ile Glu Ile Gly Glu Lys Arg Val Ile Ala Phe Asn Gly Ala Gly
    290                 295                 300

Leu Ser Val Ala Pro Glu Ile Ser Phe Glu Glu Ile Ala Ala Thr His
305             310                 315                 320

Lys Asn Pro Glu Glu Val Arg Glu Ala Tyr Ser Lys Ala Leu Phe Asp
            325                 330                 335

Ser Val Ala Met Gln Tyr Asn Val Leu Lys Thr Ala Ile Ser Gly Lys
            340                 345                 350

Gln Gly Leu Gly Ala Ser Thr Ala Asp Val Ser Leu Ser Gln Pro Trp
            355                 360                 365
```

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:11:

TTGCTGCAGG AATGGAAGAA                                                       20

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:12:

GAGAGCCTTT TGAYTACTAC A                                                    21

(2) INFORMATION FOR SEQ ID NO:13:

(i) SEQUENCE CHARACTERISTICS:
        (A) LENGTH: 24 base pairs
        (B) TYPE: nucleic acid
        (C) STRANDEDNESS: single (D) TOPOLOGY: linear (ii) MOLECULE TYPE: other nucleic acid
        (A) DESCRIPTION: /desc = "Primer"

(xi) SEQUENCE DESCRIPTION: SEQ ID NO:13:

TGTGTTTATT CGAAAAAGCA CATG                                          24

(2) INFORMATION FOR SEQ ID NO:14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:14:

CATGTGCTTT TTTGARTAAA CACA                                          24

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:15:

GAAGAAGCAT CAAAGGGTGC                                               20

(2) INFORMATION FOR SEQ ID NO:16:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:16:

GGAGGGGGCA TKATGTCAT                                                19

(2) INFORMATION FOR SEQ ID NO:17:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

TGACGCATGC GCTAGCCACT CTCGCACTTA TCGTAACGTT CGT                     43

(2) INFORMATION FOR SEQ ID NO:18:

(i) SEQUENCE CHARACTERISTICS:
        (A) LENGTH: 28 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO:18:

TGACGCATGC GCTAGCCGTT CTCGCACT                                              28

(2) INFORMATION FOR SEQ ID NO:19:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:19:

CAGCTCTTCT GCAGAACGAA CGTTACGATA                                            30

(2) INFORMATION FOR SEQ ID NO:20:

(i) SEQUENCE CHARACTERISTICS:
         (A) LENGTH: 4 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:20:

Gln Leu Leu Arg
1

(2) INFORMATION FOR SEQ ID NO:21:

(i) SEQUENCE CHARACTERISTICS:
         (A) LENGTH: 4 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:21:

Met Ala Ser His
1

(2) INFORMATION FOR SEQ ID NO:22:

(i) SEQUENCE CHARACTERISTICS:
         (A) LENGTH: 39 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:22:

ACGGGCATGC GCTAGCCACT CCCGCAAATT TCTCGATGT                                  39

(2) INFORMATION FOR SEQ ID NO:23:

(i) SEQUENCE CHARACTERISTICS:
         (A) LENGTH: 29 base pairs
         (B) TYPE: nucleic acid
         (C) STRANDEDNESS: single
         (D) TOPOLOGY: linear -continued (ii) MOLECULE TYPE: DNA (genomic)

(xi) SEQUENCE DESCRIPTION: SEQ ID NO:23:

CCATTCCTGC AGCAACATTT GGAGGCAGC  29

(2) INFORMATION FOR SEQ ID NO:24:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:24:

Gln Pro Ala His
1

(2) INFORMATION FOR SEQ ID NO:25:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

ACGAGCTCGG GATCATCATA CATGTGCTT  29

(2) INFORMATION FOR SEQ ID NO:26:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:26:

AGAGAAGCTT GATCATGAGC GGAGAATTAA  30

(2) INFORMATION FOR SEQ ID NO:27:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:27:

AGAGTCTAGA GATCCGGTGC AGATTATTTG  30

DNA STRANDS CODING FOR GLYCEROL-E-PHOSPHATE ACYLTRANSFERASE

TECHNICAL FIELD

The present invention relates to a DNA strand having the ability to biotechnologically produce a chimeric glycerol-3-phosphate acyltransferase, referred to hereinafter as ATase, between the two kinds of ATases as produced by a spinach (*Spinacea oleracea* L.) and a squash (*Cucurbita moschata* Duch.).

BACKGROUND ART

Lipids constituting the biomembranes of plants changes from the liquid crystal form into the solid form depending on the lowering of surrounding temperature, and the properties of the biomembranes are also changed therewith. It is believed in the solid state that the membrane losses the selectivity of material permeability, become incapable of effecting the essential functions, and thus the cells are impaired. Among the lipids, phosphatidyl glycerol, referred to hereinafter as PG, is a lipid easily solidified at a high temperature which has a high transition temperature from the liquid crystal to the solid state. Thus, the sensitivity of the biomembrane to temperature varies depending on the properties of PG. In this connection, the easy solidification property of PG is determined by the kinds of fatty acids as the constituents of it. The transfer of the fatty acid to glycerol-3-phosphate, referred to hereinafter as G-3-P, is carried out by G-3-P acyltransferase, referred to hereinafter as ATase, of chlorophyll. In other words, the transfer reaction of the fatty acid portion from the complex of the fatty acid and an acyl carrier protein, referred to hereinafter as ACP, to the G-3-P is catalyzed by the ATase.

In plants, the synthesis of fatty acids is carried out solely in chlorophyll, and the complex of the fatty acid and the ACP as the substrate of the ATase comprises primarily palmitoyl-ACP, referred to hereinafter as 16:0-ACP, and oleoyl-ACP, referred to hereinafter as 18:1-ACP. The selection of the substrates by the ATase is determined by the properties of the ATase itself, that is the substrate selectivity of the ATase. The substrate selectivities of the ATase have been examined in a variety of plants. For example, the ATases of spinach and pea as chilling resistant plants have high substrate specificity to 18:1-ACP, and the PG of these plants are in the liquid crystal state even at a relatively low temperature (Eur. J. Biochem. 129 (1983) 629–636). By contrast, the ATase of a chilling sensitive plant such as squash cannot distinguish 16:0-ACP and 18:1-ACP and transfer the fatty acids in respective complexes at the substantially equal ratio, so that the PG of the squash solidifies at a relatively high temperature (as described in detail below). Further, on measuring the substrate selectivities, the selectivities of fatty acid thioesters can be examined with either case of using ACP and CoA (Coenzyme A) (Plant Physiol. 83 (1987) 676–680).

Among the ATases of the chilling resistant plants, only the ones of *Arabidopsis thaliana* (Japanese Patent Laid-Open Publication No. 11891/1992; Japanese Patent Application No. 4782/1990), pea (Plant Mol. Biol. 17 (1991) 1067–1076) and spinach disclosed by the present inventor (WO 95/14094, International Application PCT/JP94/01956) have the overall amino acid sequences which have been completely elucidated. It has been revealed that the integration of an ATase gene derived from *Arabidopsis thaliana* as a chilling resistant plant or from squash as a chilling sensitive plant into tobacco as a plant having medium temperature sensitivity by the technology of genetic engineering permits the temperature sensitivity of tobacco to change into further chilling resistant in the case of the *Arabidopsis thaliana* and into further chilling sensitive in the case of the squash (Japanese Patent Publication No. 504439/1994; Japanese Patent Application No. 502792/1992).

DISCLOSURE OF THE INVENTION

It is known that the substrate selectivities of spinach ATase to unsaturated fatty acid ester (18:1-ACP) are higher than those of pea or *Arabidopsis thaliana*. Also, the amino acid sequences of the ATase derived from the other plants such as squash, cucumber or safflower which are not chilling resistant have been reported. If a gene can be created which has a substrate selectivity to 18:1-ACP higher than that of the conventionally known gene for the purpose of affording low-temperature resistance to a chilling sensitive plant, it can be expected that the gene is introduced into the plant to afford stronger chilling resistance to it.

The object of the present invention is to provide a DNA strand having the ability to biotechnologically produce an ATase useful for converting the PG in membrane lipids into the one having a stronger chilling resistant property.

The inventors have successfully obtained a gene of a chimeric ATase utilizing an unsaturated fatty acid ester as a substrate and having a higher reactivity than that of a naturally occurring ATase derived from spinach by comparing the DNAs and amino acid sequences of spinach as a typical chilling resistant plant and of squash as a chilling sensitive plant and preparing a gene (chimeric gene) in which these two genes are combined and blended with each other. The present invention has been accomplished on the basis of such informations as described above.

That is to say, the DNA strand having the ability to biotechnologically produce glycerol-3-phosphate acyltranspherase according to the present invention is characterized by having a nucleotide sequence encoding a polypeptide with a glycerol-3-phosphate acyltranspherase activity and with the amino acid sequence corresponding substantially to the amino acid sequences shown in SEQ ID NOS 1 and 2, 3 and 4, 5 and 6, 7 and 8, or 9 and 10.

Introducing the DNA strand according to the present invention into a variety of plants and expressing the DNA therein make it possible to vary the property of the PG, in a preferred embodiment, to produce chilling resistant type of plants such as spinach etc. or the further chilling resistant type of plants, that is, to obtain chilling resistant plants. The technique for introducing and expressing the DNA strand in plants is a common technique which has already been conducted in many plants such as tobacco, petunia, chrysanthemum, carnation, potato and rice.

The present invention also relates to a transformed plant and a process for preparing it. That is to say, the transformed plant and a process for preparing it according to the present invention are as follows.

A plant having the content of unsaturated fatty acids in fatty acids bound to the lipids varied from the original composition owing to the DNA described above incorporated and the glycerol-3-phosphate acyltransferase produced by the expression of the DNA.

A process for varying the composition of the fatty acids in the lipids in a plant, comprising incorporating the DNA described above into a plant cell and expressing the DNA in the plant to produce the glycerol-3-phosphate acyltransferase, so that the content of unsaturated fatty acids in fatty acids bound to the lipids in the plant is varied from the original composition.

A process for varying the sensitivity of a plant to a low temperature, comprising incorporating the DNA described above into a plant cell and expressing the DNA in the plant to produce the glycerol-3-phosphate acyltransferase, so that the composition of fatty acids bound to PG contained in the biomembrane of plant cells is varied, thus varying the content of unsaturated molecule species.

BRIEF DESCRIPTION OF DRAWINGS

FIG. 1 is schematic illustrations of ATases of spinach (PPP), squash (QQQ), and primary chimeras.

Figure 2:
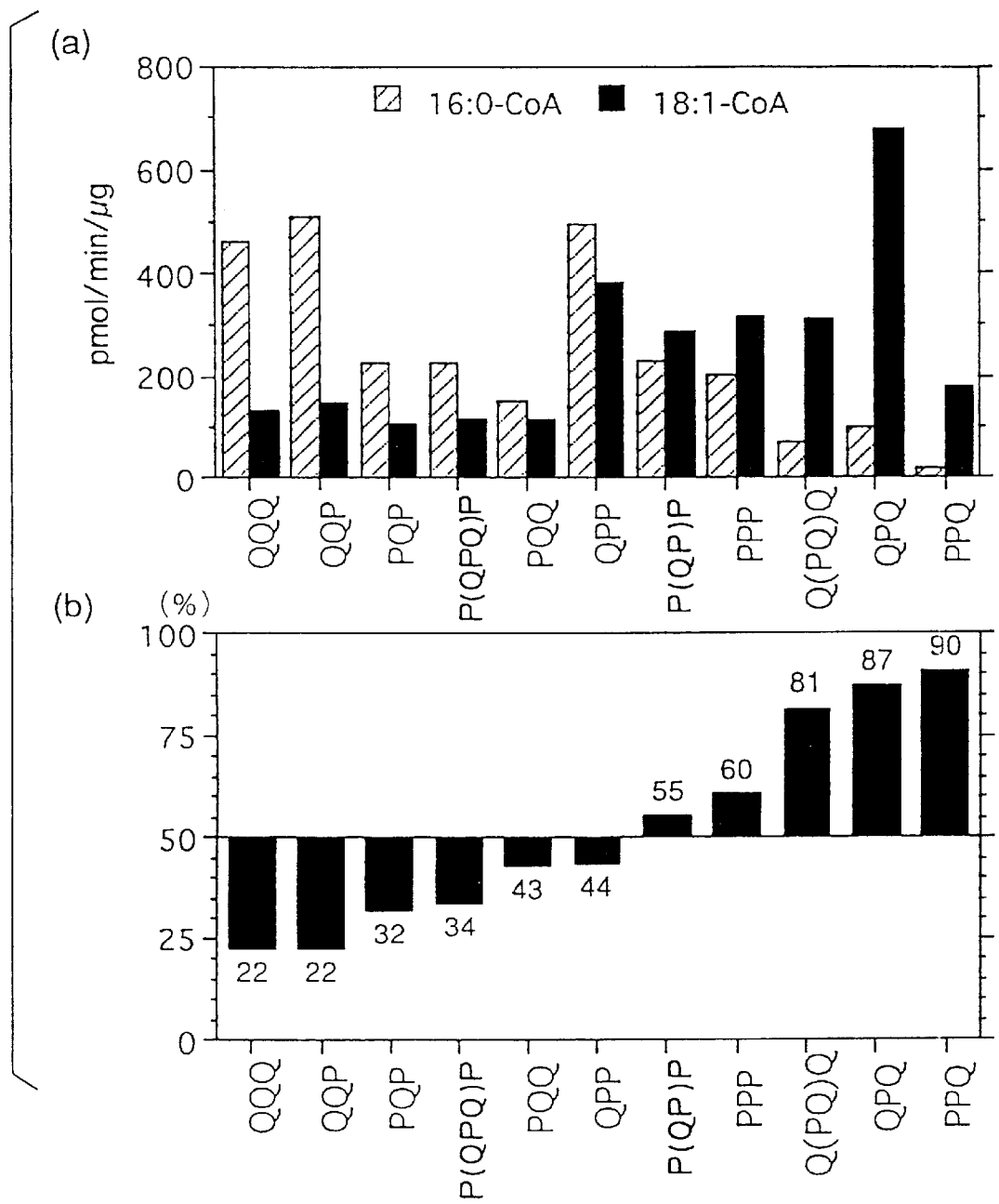

The chimeric ATases obtained by the DNA strands of the present invention are QPQ, Q(PQ)Q and PPQ, and the sites recognized by the restriction enzymes employed for the preparation of chimeras are also illustrated.

FIG. 2 is an illustration, for activities of the naturally occurring and chimeric ATases, shown with raw data (a) and with the relative values (b) of the incorporated amounts of 18:1-CoA into G-3-P to the total incorporated amounts of 16:0-CoA and 18:1-CoA.

FIG. 3 is the restriction enzyme maps of the chimeric ATase genes QPQ, Q(PQ)Q and PPQ.

Arrows show the directions of translation, and white parts represent the DNA portions derived from spinach with black parts derived from squash.

BEST MODE FOR CARRYING OUT THE INVENTION

ATase Genes

Definition

The DNA strand having the ability to biotechnologically produce ATase according to the present invention, that is the ATase gene comprises a nucleotide sequence coding for a polypeptide which has the ATase activity and amino acid sequence corresponding substantially to the one of the amino acid sequences shown in SEQ ID NOS 1 and 2, 3 and 4, 5 and 6, 7 and 8, or 9 and 10. The term "DNA strand" herein means a polydeoxyribonucleic acid having a certain length. The "DNA strand" in the invention is specified by the amino acid sequence (including the altered or modified ones as described hereinafter) of the polypeptide for which the DNA strand codes, and the polypeptide is limited as described above, so that the "DNA strand" (including the degenerated isomers as described hereinafter) is limited as well. However, the "DNA strand" contains the gene coding for the ATase and thus useful for the biotechnological production of the polypeptide, which is not possible with the only DNA strand having the limited length, but possible with the DNA strand having linked DNA strands having an appropriate length thereto at the upstream of its 5' side and at the downstream of its 3' side.

Therefore, the term "DNA strand" in the present invention includes in addition to the DNA strands having the particular lengths (SEQ ID NOS: 1, 3, 5, 7 or 9) those in the form of linear or circular DNA strands having these DNA strands having the particular lengths as a member.

A typical existence form of the DNA strands according to the present invention is a form in which the DNA strand is inserted as a part of the members in a plasmid or phage DNA, and a form in which the DNA strand is present in a microorganism (particularly bacterium), phage particle or plant in the form of being inserted in a plasmid, phage or genomic DNA. It goes without saying that the term bacterium herein includes *Escherichia coli* and Agrobacterium.

A preferred occurring form of the DNA strands according to the present invention is the one present in a plant as a form in which the ATase gene is integrally ligated to components for expression such as a promoter, a DNA strand coding for a translation regulating region, a DNA strand coding for a transit peptide into chloroplasts, the DNA strand according to the present invention, a translation terminating codon and a terminator so that the ATase gene can be stably expressed in the plant, and the integrated DNAs being inserted in a genome. As the components, known components for expression such as a promoter (e.g. cauliflower mosaic virus 35S promoter), a DNA strand coding for a translation controlling region, a DNA strand coding for a transit peptide into chloroplasts (e.g. ribulose bisphosphate carboxylase/ oxygenase small subunit), a translation terminating codon, a terminator (e.g. noparin synthase) can be used in an appropriate combination thereof.

Gene Coding Polypeptide

The DNA strands according to the present invention, as described above, are defined by the amino acid sequences for which the DNA strands code. The polypeptide is a polypeptide which has an ATase activity and whose amino acid sequence corresponds substantially to the one shown in SEQ ID NOS 1 and 2, 3 and 4, 5 and 6, 7 and 8, or 9 and 10. The phraseology "amino acid sequence corresponds substantially to the one shown in SEQ ID NOS 1 and 2, 3 and 4, 5 and 6, 7 and 8, or 9 and 10 herein indicates that the polypeptide may have a modification or alteration such as a deletion, a substitution, an insertion or an addition for some of the amino acids as long as the polypeptide has the ATase activity.

The ATase as the object in the present invention is an enzyme defined by EC2.3.1.15.

Nucleotide Sequence of the DNA Strand

The DNA strands coding for the ATase according to the present invention are described above, and their typical examples are the ones having the nucleotide sequences shown in SEQ ID NOS: 1, 3, 5, 7 or 9 or degenerated isomers thereof as well as the ones having the nucleotide sequences corresponding to the variation of the amino acid sequence of the ATase as described above or degenerated isomers thereof. The term "degenerated isomers" herein means a DNA strand which is different only in the degenerated codon and can code for the same polypeptide. For example, the DNA strand having the nucleotide sequence of SEQ ID NOS: 1, 3, 5, 7 or 9 in which a codon corresponding to any one of the amino acids, for example the codon (AAC) corresponding to Asn has been changed into a codon such as AAT which has a relationship of degeneracy therewith is herein designated a degenerated isomer.

A preferred specific example of the DNA strand according to the present invention is a DNA strand having at least one terminating codon (e.g. TAG) flanking the 3'-terminal. Also, a DNA strand in a certain length as a non-translational region may be linked to the upstream of the 5'-side and/or the downstream of the 3'-side of the DNA strand of the present invention.

Acquisition of the DNA Strand

A method for acquiring the DNA strand having the nucleotide sequence which codes for the amino acid sequence of the ATase described above comprises the chemical synthesis of at least a part of the DNA strand according to the method for the synthesis of a nucleic acid.

In consideration of that the number of the amino acid residues of the known ATase is at least 368, it is preferable to obtain the library of a DNA complementary to mRNA by the conventional method used in the field of genetic engineering, for example by the OKAYAMA-BARG method (Molecular Cell Biol. 2 (1982) 161–170) from the mRNA derived from the leaves of spinach and squash rather than by the chemical synthesis, and to create a chimeric gene which is a combination of DNAs derived from the both plants after the acquirement with the conventional method such as the immunological method with an appropriate probe or the hybridization method.

ATase genes have hitherto been isolated from six plants including spinach and squash, and their DNA structures have been elucidated. The inventors have cloned the cDNAs of spinach and squash and recombined the two genes at the restriction enzyme recognition sites in the DNA sequence common to these two cDNAs to create a chimeric gene between the both genes.

Specifically, cDNAs derived from spinach and squash were divided into three approximately equal parts with two restriction enzymes KpnI and HindIII, and chimeric genes of various combinations between both cDNAs were prepared with these divided parts. The inventors have found that among a variety of chimeric genes, a chimeric gene in which the middle fragment of the three divided parts of the squash cDNA has been replaced with the corresponding fragment of the spinach DNA (QPQ, corresponding to SEQ ID NOS: 3 and 4), and a chimeric gene in which the divided fragment at the 3' terminal of the cDNA of spinach has been replaced with the corresponding fragment of the cDNA of squash (PPQ, corresponding to SEQ ID NOS: 1 and 2) as well as a chimeric gene in which only half at the amino terminal side of the part derived from the cDNA of spinach in the chimeric gene (QPQ) of SEQ ID NOS: 3 and 4 has remained to be derived from spinach and the remaining half has been derived from squash (SEQ ID NOS: 5 and 6: Q(PQ)Q) express ATase proteins having a high substrate-specificity to unsaturated fatty acids, and accomplished the present invention on the basis of the informations.

The structure and the method for obtaining the cDNA of the ATase derived from squash are known, and thus the cDNA can be obtained according to the method (Japanese Patent Laid-Open Publication No. 235594/1989). Also, the structure and the method for obtaining the cDNA of the ATase derived from spinach have been elucidated by the present inventors, and thus the cDNA can be obtained according to the method (WO 95/14094; PCT/JP94/01956).

In addition, the general method for preparing chimeric genes including the ligation of fragments of genes can be referred to for example Molecular Cloning, Second edition, Sambrook et al. eds., Cold Spring Harbor Laboratory Press, 1989, and specific examples of the preparation of the chimeric genes according to the present invention is illustrated in the examples mentioned hereinafter.

Transformation

As described above, the DNA strands for encoding the chimeric ATases derived from spinach and squash have been provided according to the present invention. In order to express the DNA strands and to produce the polypeptides (ATase) for which the DNA strands code, it is required to be introduced into plant cells in the form that in addition to the DNA strands according to the present invention, an appropriate promoter, a DNA strand coding for a transit peptide into chloroplasts, and expression regulating sequences such as a translation termination codon and a terminator have been ligated integrally. A transformed plant can be obtained by introducing the DNA strand of the present invention into the plant cell (transformation) and culturing the cell with an appropriate combination of a promoter such as the 35S promoter of a cauliflower mosaic virus, the promoter of a nopaline synthetase, or the promoter of a small subunit of ribulose-1,5-bisphosphate carboxylase/oxygenase, and a terminator such as the terminator of the nopaline synthase, or the terminator of an octopine synthase according to the known method. It is also possible to employ the known DNA strand for encoding the transit peptide into chloroplast for example the gene of the small subunit of the ribulose-1,5-bisphosphate carboxylase of pea.

As described below, the content of unsaturated fatty acids in the fatty acids of PG depending on the differences of the expressions of genes in plant species or strains can be varied (increased or decreased) by introducing the DNA strands of the present invention into plants, and a chilling resistant plant can be obtained by increasing the content of the unsaturated fatty acids.

Plants as the object for introducing the DNA strand of the present invention may be any one of a chilling sensitive plant, a chilling resistant plant or an intermediate plant of the two, and among these plants the chilling sensitive plant is particularly preferred.

The chilling resistant plant includes cereals such as rice and corn, potatoes such as taro and sweet potato, vegetables such as cucumber, pimiento, eggplant and squash, fruit trees such as banana and melon, flowering plants such as orpine, cyclamen, lily and rose, and minor farm products such as a castor oil plant or sponge gourd. The chilling resistant vegetable and the intermediate vegetable include barley, spinach, pea, *Arabidopsis thaliana*, tomato and tobacco.

As the method for introducing exogenous genes into plants, various methods which have already been reported and established such as the method in which the Ti plasmid of Agrobacterium is used as a vector, or the method in which genes are introduced into the protoplast of the plant by electroporation can be used appropriately depending on the vegetables into which genes are intended to be introduced (e.g. see "Plant Molecular Biology Manual" Second edition, S. B. Gelvin and R. A. Schilperoort, Kluwer Academic Publishers, 1995). As the materials of plants for introducing exogenous genes, it is possible to select the appropriate one from various materials such as a leaf piece, a stem piece, a tuber piece, a protoplast, a callus, a pollen, and a pollen tube.

In the preferred embodiment of the present invention, the saturated molecular species of phosphatidyl glycerol, i.e. lipid molecular species which cause the phase separation of a biomembrane and thus the chilling injury to plants can be considerably reduced (the content of unsaturated molecular species or unsaturated fatty acids is increased), so that a chilling resistant plants are thus obtained.

EXAMPLES

The present invention is now described in more details below with reference to examples, it is not limited to these examples.

Examples

Preparation of Chimeric ATase Gene

The cDNAs derived from squash and spinach were prepared according to the method described above (Japanese Patent Laid-Open Publication No. 235594/1989, and WO 95/14094: PCT/JP 94/01956), and cloned at the EcoRI site of pTZ18R.

(1) Preparation of the ATase Gene of Squash
(i) Acquisition of RNA

The total RNA was obtained by the method described by Chirgwin et al. (Biochemistry 18 (1979) 5294–5299) from about 10 g of cotyledons which were obtained by sprouting the seeds of squash in the dark at 30° C. for 5 days and irradiating white light for 12 hours. The RNA having poly A was isolated from the total RNA according to the method described by Aviv et al. (Proc. Natl. Acad. Sci. USA, 69 (1972) 1408–1412).

(ii) Preparation of RNA Library Complementary to RNA

The DNA complementary to the above described RNA having poly A was synthesized according to the method described by Gubler et al. (Gene, 25 (1983) 263–269). In this case, oligo (dT) and random oligonucleotides were used as primers. The double stranded DNA thus synthesized was methylated with an EcoRI methylase at the cleavage site by the restriction enzyme EcoRI, and an EcoRI linker (dGGAATTCC; TAKARA SHUZO K.K.) were linked to the ends of the DNA. Furthermore, the extra part of the linker was cleaved with a restriction enzyme EcoRI, free linkers were removed from the cDNA fraction by the gel filtration method, and the cDNA and a phage λgt11 arm were linked together. The DNA was next packaged into λ phage particles by the in vitro packaging method to give a library with λgt11.

(iii) Screening of ATase Gene Retaining Strains

A strain reacting with an antiserum specific to the squash ATase 3 was selected from the phage library thus obtained as described above to obtain an ATase gene retaining strain.

The cDNA library thus obtained was first infected with the *Escherichia coli,* strain Y1090 to search about 150 plates having formed 10,000 plaques per plate thereon by the method described by Huynh et al. (DNA Cloning (1985) IRL, Oxford, Vol. 1, 49–78). Each plate was retained in tight contact with a cellulose filter which had been preliminarily dipped with isopropyl β-D-thiogalactopyranoside at a temperature of 37° C. for 2 hours, and then washed three times with 0.15 M NaCl and 50 mM phosphate buffer containing 0.1% Triton X-100 (pH 6.8) for 20 minutes. Next, the antiserum obtained from mice was diluted 1,000 times with the same buffer as described above, and the nitrocellulose filter was impregnated into the dilution and shaken at 4° C. overnight. The nitrocellulose filter was then washed three times with the buffer described above, reacted with a secondary antibody linked with a peroxidase derived from horseradish thereto at room temperature for 2 hours, and washed three times in the same manner as described above. Next, color development was carried out with 4-chloro-1-naphthol and hydrogen peroxide as the substrates, and the transformant strain which developed a strong color was taken out to carry out secondary selection with antibodies. First, the protein produced by each transformant strain was fixed on a nitrocellulose filter, and it was reacted with an antiserum. The antibodies left on the filter after washing are the ones which react only with proteins produced specifically by the transformant strains. The antibody was dissociated from the filter with 5 mM glycine-HCl (pH 2.3) and 0.15 M NaCl, and subsequently the purified ATase 3 was subjected to SDS-electrophoresis, followed by the reaction with the blotted filter. It was judged that the transformant strain in which an antibody reacting with the purified ATase 3 has been obtained is the ATase producing transformant strain. From the strain was prepared a large amount of phage, of which DNA was digested with an restriction enzyme EcoRI to cut out the foreign DNA, which has a size of about 400 bp.

The clone was subjected to nick translation with $^{32}$P-dATP (TAKARA SHUZO K.K.) to prepare a probe having a radioactivity of about $10^7$ dpm/μg. The complementary DNA library was screened again with this probe. The filter having adsorbed the phages thereon was remained in a suspension containing 50% formamide, 5× Denhardt's solution (0.1% Ficoll®, 0.1% polyvinylpyrrolidone, 0.1% bovine serum albumin), 5× SSPE (0.75 M NaCl, 50 mM sodium phosphate, 5 mM EDTA, pH 7.4), 0.1% SDS and 100 μg/ml of salmon sperm DNA overnight at 42° C. The DNA probe labelled with $^{32}$P was added for the hybridization for further 24 hours. The filter was washed according to the conventional method to select a phage which hybridizes strongly with the probe. It was estimated that this phage comprises the 1426 bp exogenous DNA in which the 1188 bp open reading frame is present, and that a protein comprising 396 amino acids and having a molecular weight of about 44,000 is encoded in this phage. The *Escherichia coli* strain (designated AT-03) which has been transformed with the transformant plasmid pAT-03 obtained by cloning the 1426 bp DNA into the plasmid vector pTZ18R (Pharmacia) has been deposited into Fermentation Research Institute, Agency of Industrial Science and Technology, M.I.T.I. (renamed National Institute of Bioscience and Human-Technology, Agency of Industrial Science and Technology), 1–3, 1-chome, Higashi, Tsukuba-Shi, Ibaraki-Ken, Japan, with the acceptance number of FERM BP-3094 (deposition date: Mar. 11, 1988)

(2) Preparation of Spinach ATase Gene
(i) Preparation of Spinach cDNA Library

Total RNA was obtained from about 10 g of the cotyledon of spinach (*Spinacia oleracea* L. var. *grabra* Viroflay/ obtained from Watabe Seed Farm (Miyagi)) according to the method described by Chirgwin et al. [Biochemistry, 18, (1979), 5294–5299]. The RNA possessing poly A [poly (A)$^+$ RNA] was isolated from the total RNA according to the method described by Aviv et al. [Proc. Natl. Acad. Sci. USA, 69, (1972), 1408–1412].

DNA (cDNA) complementary to the poly (A)$^+$ RNA was synthesized according to the method described by Gubler et al. [Gene, 25, (1983), 263–269]. In this case, oligo (dT) and random oligonucleotide were used as the primers. The double stranded cDNA thus synthesized was treated with EcoRI methylase to methylate the cleavage site with the restriction enzyme EcoRI, and then the EcoRI linker (dGGAATTCC; TAKARA SHUZO K.K.) was added to the both terminals. The surplus of the linker was cut away with the restriction enzyme EcoRI, free linkers were removed from the cDNA fraction by gel permeation method, and cDNA was linked to the arm of the phage λgt11. Subsequently, the DNA was packaged in the λ phage particles (Gigapack Gold; Stratagene) to give the spinach cDNA library in the phage λgt11.

(ii) Preparation of a Probe for Screening Library

Spinach mRNA was analyzed by the northern blot technique with the cDNAs of the ATases of squash and *Arabidopsis thaliana* as the probes. The mRNA was prepared according to the method described above. Five μg of each of the poly (A)$^+$ RNAs of squash, spinach, barley, rice and pea was denaturated with glyoxal, subjected to electrophoresis on 1.5% agarose gel, and the isolated poly (A)$^+$ RNA was transferred to a nylon membrane (GeneScreen Plus; DuPont) and hybridized with the cDNA as the probe. Hybridization was carried out in a solution comprising 6× SSPE [1× SSPE: 10 mM phosphate buffer (pH 7.0), 1 mM EDTA, 0.15 M NaCl], 0.2% SDS, and 100 μg/ml of herring sperm DNA at 60° C. for 16 hours. The membrane was then washed with shaking with 2× SSC (1× SSC: 0.15 M NaCl, 15 mM sodium citrate) twice at room temperature for 15 minutes and then twice at 42° C. for 15 minutes. As a result, when using the cDNAs of the ATases of squash and *Arabidopsis thaliana* as the probes, an about 2 kb band was detected in both of the mRNAs of squash and pea, while no band was detected in the mRNA of spinach. It was thus judged difficult to obtain the cDNA of the ATase of spinach by the screening with use of the cDNAs of the ATases of squash and *Arabidopsis thaliana* as the probes.

The comparison of the amino acid sequences of the ATases derived from these four vegetables (the DNA structures of the ATases derived from the remaining two vegetables have also been elucidated) has revealed that several regions have relatively high homology. Thus, DNA was synthesized from each of such highly homologous region found in the four vegetables of pea and cucumber in addition to *Arabidopsis thaliana* and squash, and the combinations of the two of these DNAs were used as the primers in order to obtain the DNA inserted by the primers by PCR (Polymerase Chain Reaction). The corresponding primer DNAs were synthesized (Model 394 DNA/RNA Synthesizer; Applied Biosystems), referred to as primers 1–6, respectively, of which sequences are shown below.

1. (SEQ ID NO:11) 5'-TTGCTGCAGGAATGGAAGAA,
2. (SEQ ID NO:12) 5'-GAGAGCCTTTTGA(T or C)TACTACA,
3. (SEQ ID NO:13) 5'-TGTGTTTATTCGAAAAAG CACATG,
4. (SEQ ID NO:14) 5'-CATGTGCTTTTTTGA(A or G)TAAACACA,
5. (SEQ ID NO:15) 5'-GAAGAAGCATCAAAGGGTGC,
6. (SEQ ID NO:16) 5'-GGAGGGGGCAT(G or T)ATGTCAT.

Among these primers, 1–3 correspond to sense chains, and 4–6 correspond to anti-sense chains. In the PCR reaction, 9 primer sets comprising components each of which is selected from each group were used. Genomic DNAs or DNAs derived from cDNA library may be used as a template used for the PCR reaction. In this case, cDNA was synthesized with a reverse transcriptase and mRNA as a template to form a cDNA/mRNA hybrid, which was used as a template. The reaction was carried out with Gen Amp™ RNA PCR Kit (TAKARA SHUZO). The synthesis reaction solution of the first cDNA strand comprises 50 mM Tris-HCl (pH 8.3), 50 mM KCl, 4 mM DTT, 80 mM MgCl$_2$, 0.8 mM dNTPs, 20 μg/ml of 6mer random oligo DNA, 20 U RNase inhibitor, 2 μg/ml of poly (A)$^+$ RNA, and 50 U of a reverse transcriptase and amounts to 20 μl in total, on which 100 μl of a mineral oil was layered for reaction at 42° C. for 1 hour. In a parallel experiment, the squash mRNA was also used as a template for control in addition to the spinach mRNA. After reaction, the reaction mixture was subjected to a temperature of 95° C. for 5 minutes to inactivate the reverse transcriptase. The aforementioned primers (20 μl) were added to the synthesis reaction solution of the first cDNA strand in order to synthesize the second strand. In this case, 35 cycles of PCR were carried out, with a cycle comprising the reaction at 95° C. for 1 minute, at 55° C. for 1 minute and at 72° C. for 2 minutes. After reaction, the mineral oil was extracted with 100 μl of chloroform to recover the aqueous layer, which was further treated with 100 μl of ether to remove chloroform. A 10 μl portion of the aqueous layer thus obtained was used for the isolation and analysis of the DNA synthesized by 1% agarose gel electrophoresis. As a result, an about 300 bp amplified DNA fragment was observed in both cases from spinach and squash mRNAs only with the primer set of 3 and 6. In the other 8 combinations, no band which had the same size as that of the amplified DNA fragment derived from the squash mRNA was observed in the DNA derived from the spinach mRNA. The amplified DNA fragment was blunted at the both terminals with the Klenow fragment and then cloned at the SmaI site of the plasmid pTZ18R (Pharmacia).

(iii) Screening of ATase cDNA-carrying Strain and Isolation of cDNA

The screening of the cDNA library was carried out with the DNA fragment thus obtained as a probe. An *Escherichia coli* strain Y1090 (r–) was infected with a transformant phage containing the spinach cDNA to prepare 40 plates having a diameter of about 15 cm on which about 30,000 plaques have been formed, and the phage was transcribed to a nylon membrane (Hybond-N+; Amersham). The probe DNA was labelled with $^{32}$P-dCTP with Multiprime DNA labelling Kit (Amersham). Hybridization was carried out with a hybridization solution having the same composition as that described in the paragraph (ii) at 65° C. for 16 hours, and final washing was carried out twice with 0.1× SSC at 50° C. for 20 minutes. Positive phages at the first screening was screened again in the same manner as above to give 3 positive phages, which was then purified in order to obtain phage DNAs. These phage DNAs were cut with EcoRI, and cDNA was subcloned to the plasmid pTZ18R (Pharmacia) to determine the nucleotide sequence. It was revealed that among the three cDNA clones thus obtained (SpAT#1–3), SpAT#1 has a length of about 1.5 kbp, and the amino acid sequence of its open reading frame, when compared with the amino acid sequence of the ATases of the other vegetables had an amino acid deletion at the N-terminal. Thus, the spinach cDNA library was screened with SpAT#1 as a probe to give an about 600 bp cDNA clone (SpAT#4). The cDNA clone as the combination of these clones (SpAT#14) has a length of 1,656 bp, in which a 1,413 bp open reading frame is present, and it is estimated that a protein comprising 472 amino acids and having a molecular weight of 52,177 is encoded in the open reading frame.

(3) Preparation of Chimeric ATase Gene

Comparison the nucleotide sequences between the cDNAs derived from squash and spinach with a software for analyzing the sequence of DNA and the like (DNASIS, ver. 3.0) revealed that about 70% of the nucleotide sequence was common on the whole. Several sites of recognizing restriction enzymes were found in the common sequence, and the sites of Hind III and Kpn I were present at the positions that divide almost equally into three portions (FIG. 1). A part of the ATase gene was successfully obtained by using the combinations of the two of the three enzymes comprising Eco RI which is the cloning site of the cDNA on the vector and the two restriction enzymes described above. A gene of which part was replaced by a gene derived from the other vegetable (chimeric gene) was prepared by replacing the part with another gene. In this case, genes derived from spinach (referred to as P) and squash (referred to as Q) are now illustrated sequentially from the N-terminal as a combination of the three one-third genes in order to illustrate chimeric genes. According to the illustrating method, natural genes derived from spinach and squash are illustrated PPP and QQQ, the genes in which one-third from the N-terminal has been replaced with each other are illustrated as QPP and PQQ, the genes in which the central part has been replaced with each other are illustrated PQP and QPQ, and the genes in which only the C-terminal has been replaced with each other are illustrated PPQ and QQP (FIG. 1).

In the practical preparation example, the cleavage of the genes derived from spinach and squash with Eco RI produces about 1.7 and 1.4 kbp cDNA fragments, respectively, and the further cutting of these fragments with Hind III results in another cleavage at the about one-third position from the N-terminal. The replacement of these parts with each other led to chimeric genes in which the one-third from the N-terminal had been replaced by the gene derived from the other vegetable (QPP and PQQ).

The six chimeric genes thus obtained and the two natural genes (PPP and QQQ) were cloned to the vector pET17b (Novagen) for expression in *E. coli,* and two DNAs was synthesized in order to remove the transit sequence (Applied Biosystem). In the case of spinach, the following two DNAs were synthesized:

5'-TGACGCATGC<u>GCTAGC</u>CACTCTCGCACTTATCGT AACGTTCGT-3' (SEQ ID NO:17), or

5'-TGACGCATGC<u>GCTAGC</u>CGTTCTCGCACT-3' (SEQ ID NO:18), wherein the double underline represents the Sph I site, and the single underline represents the Nhe I site; referred to hereinafter as synthetic DNA 1. The former DNA is more preferred.

5'-CAGCTCTTCTGCAGAACGAACGTTACGATA-3' (SEQ ID NO:19), wherein the swung underline represents the Pst I site. After annealing the DNAs in the equimolar amount, the fill-in reaction was carried out with the Klenow fragment of DNA polymerase in the presence of four dNTPs to prepare an adapter having the Nhe I site therein. Also, in the case of using the latter short synthetic DNA, it was combined with the synthetic DNA having the Pst I site and used as a primer for PCR in which the cDNA of the spinach gene (PPP) was used as a template, and the DNA fragment was amplified with Taq polymerase in the presence of the four dNTP. In either of these cases, cutting was carried out with Sph I and Pst I, the DNA fragment was inserted into a plasmid containing the ATase cut with the same restriction enzyme set to select a plasmid into which the Nhe I site had been introduced. As a result, the amino acid sequence in the neighborhood of the N-terminal of the maturation enzyme of the spinach ATase was changed from Gln-Leu-Leu-Arg (SEQ ID NO:20) into Met-Ala-Ser-His(Arg) (SEQ ID NO:21) (alteration of four amino acids).

On the other hand, for the gene having the squash ATase at the N-terminal, the site of the restriction enzyme Nhe I was introduced into the neighborhood of the maturation enzyme of the ATase by PCR. That is to say, after the following two DNAs were synthesized, 30 cycles of PCR were carried out, with a cycle comprising the reaction at 95° C. for 1 minute, at 55° C. for 1 minute and at 72° C. for 2 minutes, to give an about 100 bp DNA fragment having the Sph I and Nhe I sites at the one side and the Pst I site at the other side.

5'-ACGGGCATGC<u>GCTAGC</u>CACTCCCGCAAATTTCTC GATGT-3' (SEQ ID NO:22), wherein the double underline represents the Sph I site, and the single underline represents the Nhe I site; referred to hereinafter as synthetic DNA 2, and

5'-CCATTCCTGCAGCAACATTTGGAGGCAGC-3' (SEQ ID NO:23), wherein the swung underline represents the Pst I site. The DNA fragment thus obtained was cut with Sph I and Pst I, and inserted into a plasmid containing the ATase cut with the same restriction enzyme set to select a plasmid into which the Nhe I site had been introduced. As a result, the amino acid sequence in the neighborhood of the N-terminal of the maturation enzyme of the squash ATase was changed from Gln-Pro-Ala-His (SEQ ID NO:24) into Met-Ala-Ser-His (SEQ ID NO:21) (alteration of three amino acids).

Next, there is a Sac I site at the center of the portion Q of the chimera PQP, and a finer chimera for the central part was prepared with this site. The following DNA was synthesized from the site corresponding to the neighborhood of the center of the spinach gene in the antisense fashion.

5'-AC<u>GAGCTC</u>GGGATCATCATACATGTGCTT-3' (SEQ ID NO:25), wherein the underline represents the Sac I site; referred to hereinafter as synthetic DNA 3.

Synthetic DNA 1 and 3 were combined, and PCR was carried out under the same condition as described in the aforementioned example with use of PPP (natural spinach gene) as a template. The DNA fragment thus produced was cut with the set of Hind III and Sac I to give a fragment of the central part of the gene derived from spinach which ranges from Sac I newly introduced artificially to Hind III. Also, after PCR with use of the squash gene as a template in the same manner as above, the DNA fragment was cut with Hind III and Sac I, and a DNA fragment which had been inserted between the recognition sites of these enzymes was obtained and recovered. These DNA fragments and a plasmid in which PQP was cut with the set of restriction enzymes Hind III and Sac I and the fragment between them was removed were combined to prepare P(PQ)P and P(QPQ) P, respectively. In this connection, the sequence derived from spinach which is present in the center of the latter chimeric gene is the sequence corresponding to the primer used in PCR. Also, the central fragment (PQ) of the chimera obtained by cutting P(PQ)P with the restriction enzymes Hind III and Kpn I was inserted in place of P which had been removed by digesting QPQ with the same set of enzymes to form Q(PQ)Q.

Plasmids in which the Nhe I site had been introduced at the N-terminal of a variety of chimeric genes thus prepared and natural spinach and squash genes were cut with Nhe I and Eco RI, and introduced into pET17b digested with the same set of the restriction enzymes.

Experimental Example 1

Expression of Chimeric ATase Gene in *E. coli*

The plasmid obtained as described above was introduced into the competent cells of the *E. coli* strain BL21 (DE3) pLysS (Novagen) prepared according to the conventional method (Molecular Cloning, pp. 250–251; 1981), and a transformant was obtained by the selection according to resistance to ampicillin. *E. coli* containing only the chimeric gene or the original plasmid pET17b was cultured in the Luria-Bertani medium containing 100 μg/ml of ampicillin and 30 μg/ml of chloramphenicol at 37° C. until absorbance at 600 nm reaches 0.7, and isopropylthiogalactoside (IPTG) was added so as the concentration to be 0.4 mM before culturing for further 3 hours. Cells were recovered by centrifugation and stored at −20° C. until they are used. It has been confirmed by measuring the activity according to the method described below that the enzyme activity will not be changed during the storage in the refrigerator for several days.

The cells having been frozen were thawed on ice, dissolved in a solution comprising 20 mM Tris-HCl (pH 8.0), 20 mM dithiothreitol, 10 mM MgCl$_2$, 1 μg/ml of DNase I, and maintained at 4° C. for 1 hour. The *E. coli* strain BL21 (DE3) pLysS used in the experiment originally produced T7 lysozyme, and thus could be lysed satisfactorily by maintaining it at 4° C. The lysate was centrifuged at 30,000×g for 10 minutes to isolate the supernatant, which was further centrifuged at 100,000×g for 1 hour to isolate the supernatant, which was used as the sample for measuring the enzyme activity.

A portion of each sample was subjected to SDS-electrophoresis to examine the amount of expressed protein. All of the transformants contained the expressed protein at about 5% of the total sample protein, and the amounts of the protein expressed are not significantly distinguished between chimeric and natural genes.

Experimental Example 2

Measurement of Enzyme Activity

The activity of ATase was measured according to the standard method described by Bertrams and Heinz [Plant Physiol., 68, (1981), 653–657] by measuring the transfer rate from acyl-CoA to [U-$^{14}$C] glycerol-3-phosphate. The standard measurement was carried out at 24° C. with 80 μl of the solution comprising 0.25 M Hepes, pH 7.4, 6 μg/ml of bovine serum albumin, 0.3 mM [U-$^{14}$C] glycerol-3-phosphate (0.9 Ci/mole), about 1 μg of the *E. coli* extract, and 0.4 mM palmitoyl-CoA or oleyl-CoA. After 8 minutes, 2.3 ml of a mixture of chloroform and methanol (1:1), 1 ml of 1 M KCl and 0.2 M $H_3PO_4$ were added and stirred sufficiently to stop the reaction. After centrifugation, 0.9 ml of the lower layer (organic layer) was recovered and mixed with the cocktail (Aquasol-2) of a liquid scintillation counter to measure the amount incorporated. In this connection, the amount of protein added to the reaction was adjusted so as to be 30% of the amount of protein exhibiting the maximum amount of incorporation by preliminarily measuring the amounts for some concentrations. As a result, while no activity was detected in the case of *E. coli* containing pET17b solely, remarkable enzyme activity was detected in the case containing a variety of chimeric and natural ATase genes (FIG. 2(*a*)). First, natural PPP and QQQ genes exhibited high activities when an unsaturated fatty acid ester (18:1-CoA) or a saturated fatty acid ester (16:0-CoA), respectively, was used for the measurement of the activity. In addition, the genes having a sequence derived from spinach (P) in the central one-third part (PPQ, PPP, QPQ, P(PQ)P, Q(PQ)Q) generally show relatively higher activities when they used unsaturated fatty acid esters, so that this sequence was thought important for the reactions using unsaturated fatty acids as a substrate. Furthermore, surprisingly, QPQ, among these genes, showed the activity 2 times or more as compared with that of the natural gene (PPP), and thus revealed that the enzyme reaction rate of this chimeric gene was enhanced by the genetic recombination.

Next, the results of FIG. 2(*a*) was represented by the relative value to the both substrates. (FIG. 2(*b*)). As a result, the chimeric gene PPQ used substantially only unsaturated fatty acids as the substrates and thus had a reaction rate to the unsaturated fatty acids faster than that of the natural gene (PPP). Similarly, chimeric genes QPQ and Q(PQ)Q had a reaction rate to the unsaturated fatty acids faster than that of the natural gene (PPP). Particularly, from the result of the last chimeric gene Q(PQ)Q, the amino-terminal half of the central part was considered important for the reactions using unsaturated fatty acids as a substrate. Also, any chimera genes have the C-terminal one-third part comprising a gene derived from squash, and thus a combination of the gene derived from spinach in the central part and the gene derived from squash in the C-terminal was thought optimal.

In this connection, FIG. 3 illustrates the restriction enzyme maps of the chimeric ATase genes (QPQ and PPQ). In the figure, the arrow illustrates the direction of translation, the clear parts represent DNA parts derived from spinach, and the black parts represent DNA parts derived from squash.

Experimental Example 3

Introduction of a Chimeric ATase Gene (PPQ) into Tobacco Cells

DNA of a chimeric ATase gene (PPQ) was introduced into tobacco cells as described in the following.

(1) Construction of a vector plasmid for expressing in plants

A binary plasmid pBI121 (Clontech) was cut with restriction enzymes Sac I and Sma I, and the terminals thus cut were blunted with a Klenow fragment and then ligated with a T4 DNA ligase. The plasmid pBI121(-GUS) thus obtained contains no β-glucuronidase gene (GUS gene) and has the sites of the restriction enzymes Xba I and Bam HI as unique sites between the 35S promoter of a cauliflower mosaic virus and a nopaline synthase (NOS) terminator.

The plasmid containing the chimeric ATase (PPQ) obtained in Example 1 was cut with a restriction enzyme Eco RI to separate the vector plasmid pTZ18R and the DNA of the chimeric ATase by the low-melting agarose gel electrophoresis, and the DNA was cut from the gel. Furthermore, the terminal cut of the DNA was blunted with a Klenow fragment. At the same time, the plasmid pBI121 (-GUS) obtained as described above was cut with a restriction enzyme Bam HI and treated in the same manner as described above to give a blunt terminal. The DNA of the chimeric ATase and the plasmid pBI121(-GUS) thus obtained were ligated with a T4 DNA ligase to give a plasmid pBI121-35SPPQ containing a 35S promoter, the DNA of the chimeric ATase and an NOS terminator. In order to replace the 35S promoter of the plasmid with an NOS promoter, the plasmid was completely cut with Xba I and then decomposed partially with an insufficient amount of Hind III to remove the 35S promoter of about 800 bp. On the other hand, for the NOS promoter, the following two primers were prepared by PCR with pBI121 as a template. In this connection, for the design of the primer, the nucleotide sequence of the NOS promoter in pBIN19 was obtained from the data base (accession number: U09365).

5'-AGAG<u>AAGCTT</u>GATCATGAGCGGAGAATTAA-3' (SEQ ID NO:26),

5'-AGAG<u>TCTAGA</u>GATCCGGTGCAGATTATTTG-3' (SEQ ID NO:27), wherein the parts of the underline correspond to Hind III and XbaI sites, respectively. The reaction product of about 300 bp was treated with these enzymes, and the promoter DNA was purified by low-melting agarose gel electrophoresis. The DNA fragment and the plasmid having removed the 35S promoter therefrom were ligated with a T4 DNA ligase to give a plasmid pBI121-NOSPPQ containing the NOS promoter, the DNA of the chimeric ATase, and the NOS terminator.

(2) Introduction of pBI121-NOSPPQ into Agrobacterium

*Agrobacterium tumefaciens* LBA 4404 (Clontech) was inoculated into a YEB medium (5 g/l of beef extract, 2 mM $MgSO_4$, pH 7.4), cultured at 28° C. for 24 hours, and the culture medium was centrifuged at 3,000 rpm at 4° C. for 20 minutes to collect cells. The cells were washed three times with 10 ml of 1 mM HEPES, pH 7.4, once with glycerol, finally suspended into 3 ml of 10% glycerol to prepare the agrobacterium cell solution for introducing DNA.

A 50 μl portion of the Agrobacterium cell solution and the plasmid pBI121-NOSPPQ were placed into a 1 μg cuvette in order to introduce the plasmid DNA into the Agrobacterium by applying electric pulse under the condition of 25 μF, 2500 V and 200Ω in an electroporation apparatus (Gene Pulser, BioRad). The cell solution was placed into an Eppendorf tube, and 800 μl of an SOC medium (20 g/l of tripton, 5 g of yeast extract, 0.5 g of NaCl, 2.5 mM KCl, pH 7.0) was added for static culture at 28° C. for 1.5 hours. A 50 μl portion of the culture medium was seeded on a YEB agar medium (1.2% of agar) containing 100 ppm of kanamycin and cultured at 28° C. for 2 days. A single colony was selected from the colonies thus obtained, and the plasmid DNA was prepared from the colony by the alkaline method. After digesting the plasmid DNA with an appropriate restriction enzyme, the DNA fragment was isolated by 1% agarose gel electrophoresis and confirmed by the Southern blot technique with a $^{32}$P-labelled chimeric ATase DNA as a probe. The Agrobacterium is referred to as ALBNSPT.

(3) Transformation of Tobacco

The Agrobacterium ALBNSPT thus obtained was shaking cultured in an LB liquid medium containing 50 ppm of kanamycin at 28° C. for 24 hours. A 1.5 ml portion of the culture medium was centrifuged at 10,000 rpm for 3 minutes to collect cells, washed with 1 ml of the LB medium to remove kanamycin, further centrifuged at 10,000 rpm for 3 minutes to collect cells, and suspended again into 1.5 ml of the LB liquid medium to form a cell solution for infection.

Next, in order to infect tobacco leaves with Agrobacterium, young tobacco leaves were collected, dipped into a 0.5% aqueous sodium hypochlorite solution for 10 minutes, washed three times with sterile water, and water was wiped off on a sterile filter paper to make leaves for infection. The leaves were aseptically cut into pieces having a size of 1 cm$^2$ with a knife, placed on an Agrobacterium cell solution with the rear side up, gently shaken for 2 minutes, then placed on a sterile filter paper to remove the surplus of the Agrobacterium. The suspension culture cells of tobacco (cultivar: Xanthi-nc) was spread over an MS-B5 medium (containing 1.0 ppm of benzyl adenine, 0.1 ppm of naphthalene acetate and 0.8% agar) (T. Murashige and F. Skoog, Plant Physiol., 15: 473, 1962) in a dish, a Whatman No. 1 filter paper (diameter 7.0 cm) was layered, and the leaves were placed with rear side up on the filter paper. The dish was sealed with a film sheet and cultured with a light cycle of lightness for 16 hours and darkness for 8 hours at 25° C. for 2 days. Subsequently, the leaves were transferred into an MS-B5 medium containing 250 ppm of CLAPHORAN (Hechst), and cultured in the same manner for 10 days to remove the agrobacterium. The callus was transferred to an MS-B5 medium containing 250 ppm of CLAPHORAN and 100 ppm of kanamycin, and cultured for further 30 days, during which the circumference of the leaves was callused, and young plants were redifferentiated from some of the calluses. The young plant was transferred onto a (plant hormone free) MS-B5 medium containing 250 ppm of CLAPHORAN and 100 ppm of kanamycin to grow the regenerated cells, and further acclimatized to soil for cultivation in a greenhouse. The tobacco cultivated in the greenhouse was used as a material for the following tests.

Experimental Example 4

Analysis of Fatty Acids in Tobacco into which a Gene (PPQ) in the Chimeric ATase has been Introduced Phosphatidyl glycerols (PG) were prepared from the transformant plant obtained in Example 3 and a control plant (tobacco in which a GUS gene has been introduced by pBI121), and the fatty acids were analyzed.

Extraction of lipids was carried out by the Bligh-Dyer method (Can. J. Biochem. Physiol., 37: 911, 1959). Isopropanol (5 ml) containing 0.1% butylhydroxytoluene were warmed at 80° C., and cells having a wet weight of 2 g were cut into pieces, quickly added to the alcohol, treated at 80° C. for 5 minutes and cooled to room temperature. The mixture of chloroform and methanol (1:2, volume ratio, 20 ml) was added, and after disrupting the cells in a homogenizer, the mixture was left standing for 15 minutes. The mixture was diluted with 12 ml of chloroform and 12 ml of distilled water, stirred vigorously, separated into the aqueous layer and the organic layer by centrifugation at 3,000 rpm and 4° C. for 30 minutes to recover the organic layer (lower layer). An appropriate amount of ethanol was added to the organic layer, and the organic solvents were removed with a rotary evaporator at 30° C. under reduced pressure. The residue was dissolved in 2 ml of a mixture of chloroform and methanol (1:4, volume ratio) and used as the total lipid extract.

In order to fractionate the lipids, the lipids were mixed with 25 ml of a suspension of DEAE-Toyopearl 650C (TOSO) and 25 ml of 1 M aqueous sodium acetate solution (pH 7.0) to form an acid type. This was washed sequentially with distilled water and methanol, suspended in methanol, charged into a column having an internal diameter of 2 cm up to a height of 1.5 cm, and further washed with 50 ml of a mixture of chloroform and methanol (1:4, volume ratio).

The total lipid extract was applied on the column, washed sequentially with 50 ml of a mixture of chloroform and methanol (1:4, volume ratio), 50 ml of acetic acid, and 15 ml of a mixture of chloroform and methanol (1:4, volume ratio) to remove most of the contaminated lipids. Then, washing with 50 ml of a 10 M aqueous ammonium acetate solution (20:80, 0.2, volume ratio) gave a lipid fraction containing PG. The fraction was diluted with 15 ml of ethanol, and the solvents were removed under reduced pressure. The residue was dissolved in 200 μl of a mixture of chloroform and methanol (2:1, volume ratio), and the lipids was separated on a silica gel-TLC plate #5721 (Merck) with a developing solvent of chloroform:methanol:acetic acid:water (50:20:10:15:5, volume ratio). After TLC separation, primulon was sprayed for fluorescent coloring under ultraviolet light, and the PG fraction having the same rate of flow as that of the authentic PG was shaven off together with silica gel and put into a screwed test tube. 2.5 ml of 5% methanolic hydrochloric acid was added, and the mixture was reacted to methylate the fatty acids. The methyl esters of fatty acids were extracted four times with hexane, and the solvent was removed under reduced pressure. Gas chromatography was used for the analysis of fatty acid methyl esters. Fractionation was carried out with a gas chromatograph GC-17AAWFW (Shimadzu Seisakusho, Ltd.), fatty acid methyl esters were identified by comparing the retention times with those of standard fatty acid methyl esters. Quantitative determination was carried out with Chromatopak C-R7A plus (Shimadzu Seisakusho, Ltd.). The results are shown in Table 1.

TABLE 1

Compositions of fatty acids and molecular species of PG in the leaves of tobacco

| Plant | 16:0 + 16:1t + 18:0 (%) | Estimated saturated molecular species (%) |
| --- | --- | --- |
| Control | 70.9 | 41.8 |
| Transformant #1 | 75.8 | 51.6 |
| Transformant #2 | 75.4 | 50.8 |
| Transformant #3 | 63.8 | 27.6 |
| Transformant #4 | 67.1 | 34.2 |
| Transformant #5 | 66.7 | 33.4 |

While the content of the saturated fatty acids (16:0+16:1t+18:0) in the fatty acids linked to PG was 70.9% in the control tobacco, the content increased in transformants #1 and 2 and decreased in transformants #3, 4 and 5 in the tobaccos into which chimeric ATase (PPQ) had been introduced. It was thus indicated that the expression of the chimeric ATase makes possible the both directions of increasing and decreasing the unsaturated fatty acids. Particularly, in the case of decreasing the unsaturated fatty acid contents, the content of the fatty acids in the transformant #3 was decreased in a proportion of 7% or more as compared with that of the control, and the saturated molecular species was also decreased to a level below 28%.

INDUSTRIAL APPLICABILITY

According to the present invention, a chimeric ATase gene having an unsaturated fatty acid ester as a substrate and a higher reactivity than that of an ATase derived from naturally occurring spinaches has been successfully obtained by comparing the DNAs and amino acid sequences of spinach as a typical chilling resistant plant and of squash as a chilling sensitive plant and preparing a (chimeric) gene in which these two genes are linked to and blended with each other at the specific regions. (It has been quite an unexpected result that the ATase obtained from the chimeric gene of the combination of a gene derived from a chilling resistant plant and a gene derived from a chilling sensitive plant has an increased substrate selectivity to unsaturated fatty acids than that of the chilling resistant plant.

Thus, the DNA strand according to the present invention is useful as a gene which is capable of affording a stronger chilling resistance to plants by introducing it into them.

What is claimed is:

1. A chimeric DNA that codes for an enzyme having glycerol-3-phosphate acyltransferase activity, the enzyme comprising a first partial amino acid sequence selected from the group consisting of position 126 (Lys) to 201 (Leu) of SEQ ID NO: 1, position 126 (Lys) to 201 (Leu) of SEQ ID NO: 2, position 126 (Lys) to 201 (Leu) of SEQ ID NO: 3, position 126 (Lys) to 201 (Leu) of SEQ ID NO: 4, position 126 (Lys) to 201 (Leu) of SEQ ID NO: 5, position 126 (Lys) to 201 (Leu) of SEQ ID NO: 6, position 126 (Lys) to 201 (Leu) of SEQ ID NO: 7, position 126 (Lys) to 201 (Leu) of SEQ ID NO: 8, position 126 (Lys) to 201 (Leu) of SEQ ID NO: 9, and position 126 (Lys) to 201 (Leu) of SEQ ID NO: 10, and a second partial amino acid sequence selected from the group consisting of position 245 (Trp) to 368 (Trp) of SEQ ID NO: 1, position 345 (Trp) to 368 (Trp) of SEQ ID NO: 2, position 245 (Trp) to 368 (Trp) of SEQ ID NO: 3, position 245 (Trp) to 368 (Trp) of SEQ ID NO: 4, position 245 (Trp) to 368 (Trp) of SEQ ID NO: 5, position 245(Trp) to 368 (Trp) of SEQ ID NO: 6, position 245 (Trp) to 368 (Trp) of SEQ ID NO: 7, position 245(Trp) to 368 (Trp) of SEQ ID NO: 8, position 245 (Trp) to 368 (Trp) of SEQ ID NO: 9, and position 245 (Trp) to 368 (Trp) of SEQ ID NO: 10, wherein the enzyme has a higher substrate selectivity for oleoyl-(acyl-carrier-protein) than for palmitoyl-(acyl-carrier-protein).

2. A chimeric DNA as described in claim 1, wherein the DNA sequence encodes a polypeptide having an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO: 10.

3. A chimeric DNA according to claim 1, wherein the nucleotide sequence encoding the polypeptide is selected from the group consisting of SEQ ID NO: 1, SEQ ID NO: 2, SEQ ID NO: 3, SEQ ID NO: 4 and SEQ ID NO: 5, or a degenerated isomer thereof.

4. A plant having an altered unsaturated fatty acid composition, wherein the plant comprises a chimeric DNA strand according to claim 1 and the DNA expresses glycerol-3-phosphate acyltransferase activity that leads to the altered unsaturated fatty acid composition.

5. A plant according to claim 4, wherein the content of the unsaturated fatty acids is increased with comparison to a plant that lacks the chimeric DNA.

6. A process for varying the composition of fatty acids in plant lipids, comprising incorporating DNA as described in claim 1 into a plant cell and expressing the DNA in the plant to produce glycerol-3-phosphate acyltransferase activity.

7. A process for varying the sensitivity of a plant to a low temperature, comprising incorporating DNA according to claim 1 into a plant cell and expressing the DNA to produce glycerol-3-phosphate acyltransferase, wherein the glycerol-3-phosphate acyltransferase varies the composition of fatty acids bound to phosphatidyl glycerol compared to fatty acids within a plant that lacks the incorporated DNA.

8. A process according to claim 6, wherein the content of the unsaturated fatty acids is increased.

9. A process according to claim 7, wherein the content of the unsaturated fatty acids is increased.

* * * * *

UNITED STATES PATENT AND TRADEMARK OFFICE
CERTIFICATE OF CORRECTION

PATENT NO. : 6,160,203
DATED : December 12, 2000
INVENTOR(S) : Stefano Ferri et al.

Page 1 of 1

It is certified that error appears in the above-identified patent and that said Letters Patent is hereby corrected as shown below:

Column 48, claim 1,
"position 345(Trp)" should read -- position 245(Trp) --.

Signed and Sealed this

Sixteenth Day of April, 2002

Attest:

JAMES E. ROGAN
Attesting Officer *Director of the United States Patent and Trademark Office*